United States Patent
Bartel et al.

(12)

(10) Patent No.: US 6,291,173 B1
(45) Date of Patent: Sep. 18, 2001

(54) MMSC2—AN MMAC1 INTERACTING PROTEIN

(75) Inventors: Paul L. Bartel; Sean V. Tavtigian, both of Salt Lake City, UT (US)

(73) Assignee: Myriad Genetics, Inc., Salt Lake City, UT (US)

(*) Notice: Subject to any disclaimer, the term of this patent is extended or adjusted under 35 U.S.C. 154(b) by 0 days.

(21) Appl. No.: 09/306,998

(22) Filed: May 7, 1999

Related U.S. Application Data

(60) Provisional application No. 60/084,740, filed on May 8, 1998.

(51) Int. Cl.[7] ............................. C07H 21/04; C12N 5/00; C12N 15/00; C12Q 1/68; G01N 33/48
(52) U.S. Cl. ........................... 435/6; 536/24.33; 536/23.5; 435/320.1; 435/325; 435/40.5; 435/69.1; 436/64
(58) Field of Search ...................... 514/44; 536/23.5, 536/24.33, 24.3; 435/320.1, 325, 69.1, 6, 40.5; 436/64

(56) References Cited

U.S. PATENT DOCUMENTS 5,585,239 * 12/1996 Lamarco et al. ..................... 435/6

OTHER PUBLICATIONS

Ullmer C et al. FEBS Lett. 424:63–68, 1998.*
Clark TM et al. Pathology Oncology Research 5:3–15, 1999.*
Anderson WF. Nature 392 (SUPP):25–30, 1998.*
Verma IM and Somia N. Nature 389:239–242. 1997.*
Orkin SH and Motulsky AG. Report and Recommendations of the Panel to Assess the NIH investment in research on gene therapy, 1995.*
Crystal RG. Science 270:404–410.1995.*
Duerr, E. et al. (1998). PTEN mutations in gliomas and glioneuronal tumors. *Oncogene* 16:2259–2264.
Grøbœk, K. et al. (1998). Alterations of the MMAC1/PTEN gene in lymphoid malignancies. *Blood* 91:4388–4390.
Dahia, P.L.M. et al. (1998). A highly conserved processed PTEN pseudogene is located on chromosome band 9p21. *Oncogene* 16:2403–2406.
Chen, J. et al. (1998). A study of the PTEN/MMAC1 gene in 136 breast cancer families. *Hum. Genet.* 102:124–125.
Whang, Y.E. et al. (1998). Inactivation of the tumor suppressor PTEN/MMAC1 in advanced human prostate cancer through loss of expression. *Proc. Natl. Acad. Sci. USA* 95:5246–5250.

* cited by examiner

*Primary Examiner*—Scott D. Priebe
*Assistant Examiner*—Ram R. Shukla
(74) *Attorney, Agent, or Firm*—Rothwell, Figg, Ernst & Manbeck

(57) ABSTRACT

The present invention is directed to the MMSC2 gene, its protein product and the use of the protein to (i) detect mutant MMAC1 proteins, (ii) screen for drugs which can be used for suppressing tumor growth and (iii) identify proteins which interact with the MMAC1 gene or are involved in the tumor suppression pathway of the MMAC1 gene.

17 Claims, 2 Drawing Sheets

MMSC2— AN MMAC1 INTERACTING PROTEIN

CROSS-REFERENCE TO RELATED APPLICATION

The present application is related to U.S. provisional patent application Ser. No. 60/084,740, filed May 8, 1998, incorporated herein by reference.

BACKGROUND OF THE INVENTION

The present invention is directed to the MMSC2 gene, its protein product and the use of the protein to (i) detect mutant MMAC1 proteins, (ii) screen for drugs which can be used for suppressing tumor growth and (iii) identify proteins which interact with the MMAC1 gene or are involved in the tumor suppression pathway of the MMAC1 gene.

The publications and other materials used herein to illuminate the background of the invention or provide additional details respecting the practice, are incorporated by reference, and for convenience are respectively grouped in the appended List of References.

A number of genetic alterations are involved in the oncogenesis of glioblastoma multiforme, including inactivation of p53, p16, RB, amplification of the gene encoding epidermal growth factor receptor and several other molecular alterations (Louis & Gusella, 1995). However the most common genetic alteration is the deletion of large regions or an entire copy of chromosome 10 (Fults et al., 1990; Rahseed et al., 1992). Recently, the tumor suppressor gene MMAC1 (Steck et al., 1997), also known as PTEN (Li et al., 1997) or TEP1 (Li & Sun, 1997) was mapped to 10q23 and shown to be mutated in 17–24% of xenografited and primary glioblastomas, 14% of breast cancer samples and 25% of kidney carcinomas (Steck et al., 1997). The mutation frequency in established cell lines of these tumor types is somewhat higher. In addition to this predicted involvement in sporadic cancer, germ-line MMAC1 mutations have been detected in two autosomal dominant disorders, Cowden disease (Nelen et al., 1997; Liaw et al., 1997), a syndrome that confers an elevated risk for tumors of breast, thyroid and skin, and Bannayan-Zonana syndrome (Marsh et al., 1997), a condition characterized by macrocephaly, lipomas, intestinal hamartomatous polyps, vascular malformations and some skin disorders. Mutations of MMAC1 in primary endometrial carcinomas (Kong et al., 1997) and in juvenile polyposis coli (Olschwang et al., 1998) have also been seen.

The predicted protein product of the MMAC1 gene has several regions of homology with other proteins. The MMAC1 protein has an amino terminal domain with extensive homology to tensin, a protein that interacts with actin filaments at focal adhesions, and with auxilin, a protein involved in synaptic vesicle transport. The MMAC1 protein also has a region with extensive homology to protein tyrosine phosphatases (Steck et al., 1997; Li et al., 1997). Mutations of MMAC1 in tumors, its cytoplasmic localization (Li & Sun, 1997) and its intrinsic phosphatase activity (Li & Sun, 1997; Myers et al., 1997) suggested that its activity could be important in some aspect of tumor progression, possibly to counteract the oncogenic effect of a specific protein tyrosine kinase. In addition, MMAC1 is rapidly down-regulated by TGFβ in cells sensitive to its cell growth and cell adhesion regulatory properties (Li & Sun, 1997).

Experiments on glioma cell growth have shown that MMAC1 is a protein phosphatase that exhibits functional and specific growth-suppressing activity. In such experiments, the introduction of HA-tagged MMAC1 into glioma cells containing endogenous mutant alleles caused growth suppression, but was without effect in cells containing wild-type MMAC1 (Furnari et al., 1997). The ectopic expression of MMAC1alleles, which carried mutations found in primary tumors and have been shown or are expected to inactivate its phosphatase activity, caused little growth suppression (Furnari et al., 1997). Although these activities of MMAC1 are known, the mechanisms of tumor suppression by MMAC1 and the interaction of the MMAC1 protein with other proteins are not well understood.

Many cytosolic signaling proteins and cytoskeletal proteins are composed of modular units of small protein-protein interactive domains that allow reversible and regulated assembly into larger protein complexes. These domains include the Src-homology SH2 and SH3 domains (Schlessinger, 1994; Pawson, 1994), pleckstrin-homology (PH) domains (Lemmon et al., 1996; Shaw, 1996), phosphotyrosine-binding (PTB) domains (Harrison, 1996; van der Greer & Pawson, 1995; Kavanaugh et al., 1995) and postsynaptic density protein, disc-large, zo-1 (PDZ) domains (Woods & Bryant, 1991; Dho et al., 1992; Woods & Bryant, 1993; Keimedy, 1995; Kornau et al., 1995). So far, PDZ domains have been found in more than 50 proteins (Tsunoda et al., 1997), and many proteins have multiple PDZ domains (Pawson & Scott, 1997). For a review of PDZ domains, as well as the other protein-protein interactive domains, see Pawson & Scott (1997).

A distinguishing feature of PDZ domains is their recognition of short peptides at the carboxyl terminal end of proteins. For example, one family of PDZ domains selected peptides with the consensus motif Glu-(Ser/Thr)-Xaa-(Val/Ile) (SEQ ID NO: 1) at the carboxy terminus whereas a second family of PDZ domains selected peptides with hydrophobic or aromatic side chains at the carboxy terminal three residues (Songyang et al., 1997). The presence of multiple PDZ domains in proteins may have at least two important consequences. An individual PDZ-containing protein could bind several subunits of a particular channel thereby inducing channel aggregations. Furthermore, the individual domains of a protein can have distinct binding specificities thereby inducing the formation of clusters that contain heterogeneous groups of proteins.

One example of this latter consequence of multiple PDZ domains is the InaD protein which contains five PDZ domains and acts as a scaffolding protein to organize the light-activated signaling events in Drosophila (Shieh & Zhu, 1996; Tsunoda et al., 1997). InaD associates through distinct PDZ domains with a calcium channel(TRP), phospholipase C-β (the target of rhodopsin-activated heterotrimeric guanine nucleotide-binding protein (Gqα) and protein kinase C.

Two further properties of PDZ domains or proteins which contain them may expand their potential activities. First, some PDZ domains may bind internal peptide sequences and, indeed, have a propensity to undergo homotypic or heterotypic interactions with other PDZ domains (Brenman et al., 1996). Second, proteins with PDZ domains frequently contain other interaction modules, including SH3 and LIM domains, and catalytic elements such a tyrosine phosphatase or nitric oxide synthase domains. PDZ domains may therefore both coordinate the localization and clustering of receptors and channels, and provide a bridge to the cytoskeleton or intracellular signaling pathways.

It is desired to determine the mechanisms of tumor suppression for MMAC1 and to identify proteins which interact with the MMAC1 protein. Such proteins can be used to assay for mutated MMAC1 proteins and/or screen potential drugs for suppressing tumor growth and/or identify additional proteins which interact with MMAC 1.

SUMMARY OF THE INVENTION

The present invention is directed to the MMSC2 gene, its protein product and the use of the protein to (i) detect mutant MMAC1 proteins, (ii) screen for drugs which can be used for suppressing tumor growth and (iii) identify proteins which interact with the MMAC1 gene or are involved in the tumor suppression pathway of the MAMC1 gene.

Using yeast two-hybrid screening, it has been found MMAC1 binds to a protein herein named MMSC2. The nucleotide sequence is set forth as SEQ ID NO:2, and the amino acid sequence is set forth as SEQ ID NO:3. It has been found that MMSC2 has 11 PDZ domains and that one or more of these domains interacts specifically with the three carboxyl terminal amino acids of MMAC1. Specifically, it has been found that PDZ domain numbers 7,10 and 13 interact with MMAC1, with 7 appearing stronger. Since MMSC2 contains 11 PDZ domains and interacts with MMAC1, a known tumor suppressor having a region of homology with protein tyrosine phosphatases, MMSC2 acts as a scaffolding protein in a common biochemical pathway with MMAC 1. These characteristics indicate that the interaction between MMAC 1 and MMSC2 is required for the tumor suppressor activity of MMAC1.

BRIEF DESCRIPTION OF THE FIGURES AND TABLES

SUMMARY OF SEQUENCE LISTING

Figure 1:
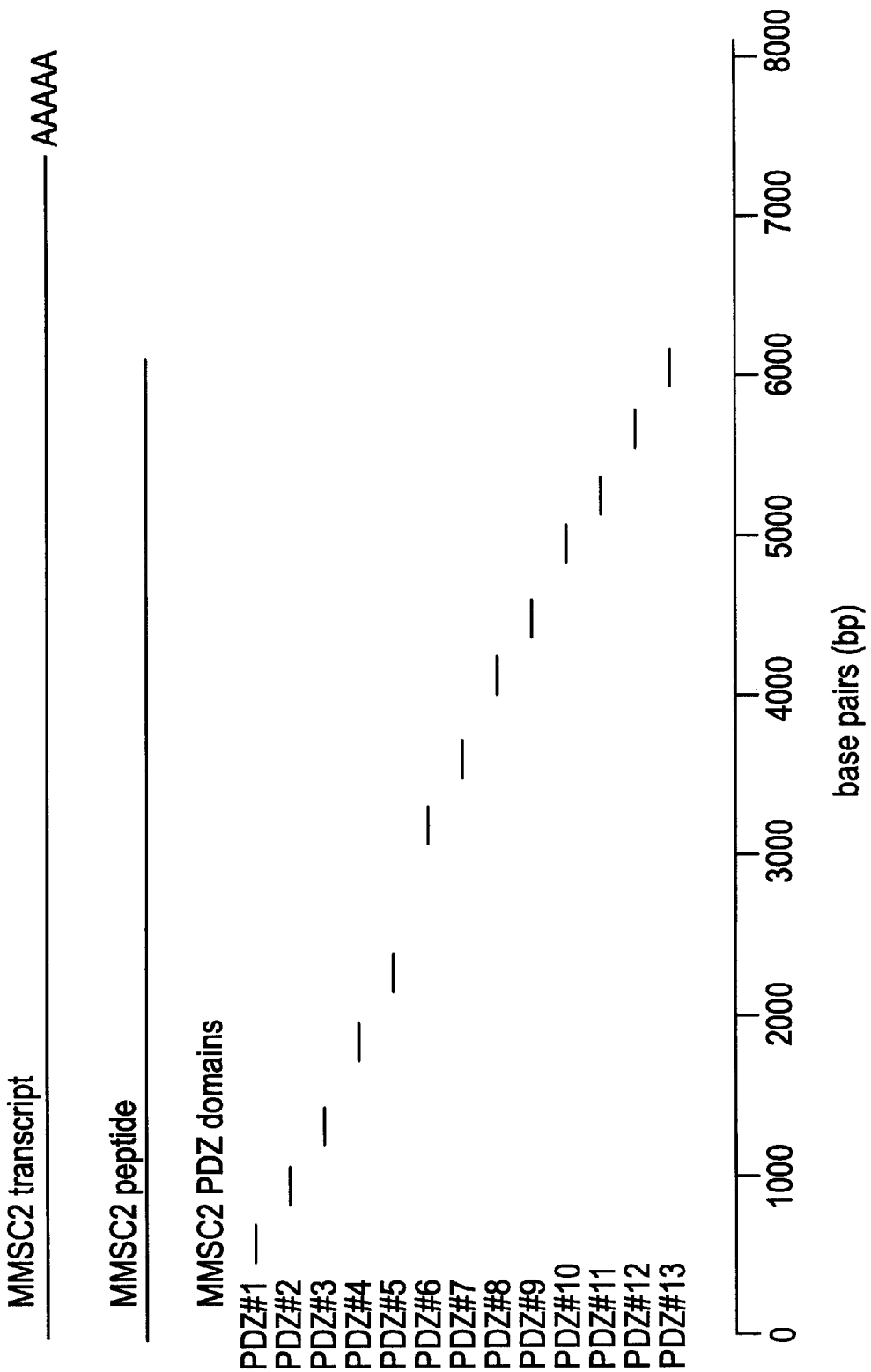
FIG. 1 shows a diagram of MMSC2 indicating the position of ORF and the positions of the 13 PDZ domains.

SEQ ID NO:1 is a consensus motif to which one family of PDZ domains interacts. SEQ ID NO:2 is the nucleotide sequence for the MMSC2 gene. SEQ ID NO:3 is the amino acid sequence for the MMSC2 protein. SEQ ID NO:4 is the 15 C-terminal amino acids of MMAC1. SEQ ID NO:5 is primer 9BP-1 F1. SEQ ID NO:6 is primer 9BP-1 R4. SEQ ID NO:7 is primer 9BP-1 #1. SEQ ID NO:8 is primer 9BP-1 #2. SEQ ID NO:9 is primer 9BP-1 #NO:10 is primer 9BP-1 #7. SEQ ID NO:11 is the SH3 binding peptide. SEQ ID NO:12 is the MMAC1 binding peptide. SEQ ID NOs:13–72 are primers for PCR amplification of the MMSC2 gene.

DETAILED DESCRIPTION OF THE INVENTION

The present invention is directed to the MMSC2 gene, its protein product and the use of the protein to (i) detect mutant MMAC1 proteins, (ii) screen for drugs which can be used for suppressing tumor growth and (iii) identify proteins which interact with the MMAC1 gene or are involved in the tumor suppression pathway of the MMAC1 gene.

Using yeast two-hybrid screening, it has been found MMAC1 binds to a protein herein named MMSC2. The nucleotide sequence is set forth as SEQ ID NO:2, and the amino acid sequence is set forth as SEQ ID NO:3. It has been found MMSC2 has 11 PDZ domains and that one or more of these domains interacts specifically with the three carboxyl terminal amino acids of MMAC1. Specifically, it has been found that PDZ domain numbers 7, 10 and 13 interact with MMAC 1 with 7 appearing stronger. Since MMSC2 contains 11 PDZ domains and interacts with MMAC1, a known tumor suppressor having a region of homology with protein tyrosine phosphatases, MMSC2 acts as a scaffolding protein in a common biochemical pathway with MMAC1. These characteristics indicate that the interaction between MMAC1 and MMSC2 is required for the tumor suppressor activity of MMAC1.

The evidence presented herein shows that the function of MMSC2 is to make a scaffold that binds to MMAC1, the phosphatase substrate(s), and the (probably oncogene) tyrosine kinase(s). Thus, a valuable drug will be one that can prevent binding of either the substrate(s) or the tyrosine kinases(s) to MMSC2.

The yeast two-hybrid screening assay described herein identified five clones encoding bonafide MMAC1-interacting proteins. These clones were named PDZBN2B, PDZBN3A, PDZBN5B, PDZBN18D, and pdzk4. Comparison of the sequences of these clones suggested that they were all partial cDNAs derived from the same novel gene. A search of GenBank with these sequences revealed strong sequence similarity with a partial mouse cDNA sequence called 9ORF binding protein 1 (9BP-1)(GenBank Accession #AF000168).

Several rounds of cDNA library screening were required to identify cDNA clones that could be assembled into the full length MMAC2 sequence. In the first round, a 509 base pair(bp) probe was developed from the 5' end of clone PDZBN2B using the primers 9BP-1 F1 and 9BP-1 R4. This probe was used to screen a human placental cDNA library and a human prostate cDNA library. Two of the informative clones obtained were p118a(placental) and pr63(prostate). A search of GenBank with this additional sequence yielded an additional human EST (GenBank Accesion #C75629). For the second round of cDNA library screening, a 202 bp probe was developed from the 5' end of this EST using primers 9BP-1 #1 and 9BP-1 #2. This probe was used to screen a human prostate cDNA library; two of the informative clones obtained were clone #10 and clone #3. For the third round of cDNA library screening, a 172 bp probe was developed from the 5' end of clone #3 using primers 9BP-1 #5 and 9BP-1 #7 and used to screen a human prostate cDNA library. One of the resulting clones, clone #6, yielded the start codon and part of the 5' UTR, including in-frame upstream stop codons. The nucleotide sequence for MMSC2 is set forth in SEQ ID NO:2 with the amino acid sequence of the encoded protein set forth in SEQ ID NO:3.

As previously noted, SEQ ID NO:2 sets forth the nucleotide sequence for MMSC2. However, it has been found that the mRNA for MMSC2 is subject to alternate splicing On the basis of the sequence for MMSC2, genomic clones have been isolated and are being analyzed to determine splice junctions and alternate splicing for the mRNA. In addition, the PDZ domains of MMSC2 are analyzed in the yeast two-hybrid assay to identify other proteins which interact with MMSC2 and consequently are involved in the MMAC1 tumor suppressor pathway.

Since MMSC2 is an MMAC1 interacting protein that is involved in tumor suppression activity in the MMAC1 pathway, mutations in the MMSC2 gene which affect the interaction of MMSC2 with MMAC 1 or affect the interaction of other proteins with MMAC1 as a result of the scaffolding effect of MMSC2 will interfere with the MMAC1 tumor suppressor pathway and lead to tumorigenesis. Thus, an additional aspect of the present invention is the screening of MMSC2 for such mutations using conventional techniques. Such methods may further comprise the step of amplifying a portion of the MMAC2 gene, and may further include a step of providing a set of polynucleotides which are primers for amplification of said portion of the MMSC2 gene. The method is useful for identifying mutations for use in either diagnosis of cancer or prognosis of cancer. Since such variants can now be detected earlier, i.e., before symptoms appear, and more definitively, better treatment options will be available in those individuals identified as having harmful mutations in MMSC2.

The present invention is directed to the determination that the MMSC2 binds to the C-terminal region of MMAC1 and is involved in a common pathway with MMAC1 which is a known tumor suppressor. Since many of the mutations in MMAC1 are frameshift or nonsense mutations which consequently alter the C-terminus of MMAC1, MMSC2 can be used to assay for normal or mutated MMAC 1 proteins using conventional techniques.

Finally, the present invention is directed to a method for screening drug candidates to identify drugs useful for treating or preventing cancer. Drug screening is performed by expressing mutant MMSC2 and assaying the effect of a drug candidate on the binding of MMSC2 with MMAC 1. Similarly, one can test the effect of a drug candidate on the binding of wild-type MMSC2 with a mutant MMAC1. Such assays can be performed in vitro or in vivo, such as in oocytes, mammalian cells or transgenic animals. Other assays may test the ability of a drug, wherein the drug may be, e.g., a peptide, to replace the activity of MMSC2 such that the drug plus MMAC1 will work in concert similar to the normal wild-type interactions of MMSC2 and MMAC1. Again, similar assays may be performed to screen for drugs which replace a mutant MMAC1 and will bind to wild-type MMSC2 to replace the MMAC1 function which is lacking as a result of a mutated MMAC1.

According to the diagnostic and prognostic method of the present invention, alteration of the wild-type MMSC2 gene is detected. In addition, the method can be performed by detecting the wild- type MMSC2 gene and confirming the lack of a cause of cancer as a result of this locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues and are not inherited in the germline. Germline mutations can be found in any of a body's tissues and are inherited. Point mutational events may occur in regulatory regions, such as in the promoter of the gene, leading to loss or diminution of expression of the mRNA. Point mutations may also abolish proper RNA processing, leading to loss of expression of the MMSC2 gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis, hybridization using nucleic acid modified with gold nanoparticles and PCR-SSCP, as discussed in detail further below. Also useful is the recently developed technique of DNA microchip technology.

The presence of cancer due to a germline mutation at this locus may be ascertained by testing any tissue of a human for mutations of the MMSC2 gene. For example, a person who has inherited a germline MMSC2 mutation, especially one which alters the interaction of MMSC2 with MMAC1, would be prone to develop cancer. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the MMAC2 gene. Alteration of a wild-type MMSC2 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of cancer cases. Southern blots displaying hybridizing fragments differing in length from control DNA when probed with sequences near or including the MMSC2 locus indicate a possible mutation. If restriction enzymes which produce very large restriction fragments are used, then pulsed field gel electrophoresis (PFGE) is employed.

Detection of point mutations may be accomplished amplification, e.g., PCR, from genomic or cDNA and sequencing the amplified nucleic acid or by molecular cloning of the MMSC2 allele and sequencing the allele using techniques well known in the art.

There are six well known methods for a more complete, yet still indirect, test for confirming the presence of a susceptibility allele: 1) single stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Rano and Kidd, 1989). For allele-specific PCR, primers are used which hybridize at their 3' ends to a particular MMSC2 mutation. If the particular mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears, SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type MMSC2 gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the MMSC2 gene can also be detected using Southern hybridization, especially if the changes are gross rearrangements, such as deletions and insertions.

DNA sequences of the MMSC2 gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified MMSC2 sequences can be performed, for example, on a nylon filter. Hybridization to a particular probe under high stringency hybridization conditions indicates the presence of the same mutation in the tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Nature Genetics, 1996). Also see Fodor (1997).

The most definitive test for mutations in a candidate locus is to directly compare genomic MMSC2 sequences from patients with those from a control population. Alternatively, one could sequence messenger RNA after amplification, e.g., by PCR, thereby eliminating the necessity of determining the exon structure of the candidate gene.

Mutations from patients falling outside the coding region of MMSC2 can be detected by examining the non-coding regions, such as introns and regulatory sequences near or within the genes. An early indication that mutations in noncoding regions are important may come from Northern blot experiments that reveal messenger RNA molecules of abnormal size or abundance in patients as compared to control individuals.

Alteration of MMSC2 mRNA expression can be detected by any techniques known in the art. These include Northern blot analysis, PCR amplification and RNase protection. Diminished mRNA expression indicates an alteration of the wild-type gene. Alteration of wild-type genes can also be detected by screening for alteration of wild-type MMSC2 protein. For example, monoclonal antibodies immunoreactive with MMSC2 can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered MMSC2 protein can be used to detect alteration of the wild-type MMSC2 gene. Functional assays, such as protein binding determinations, can be used. In addition, assays can be used which detect MMSC2 biochemical function. Finding a mutant MMSC2 gene product indicates alteration of a wild-type MMSC2 gene. One such binding assay is the binding of MMSC2 with wild-type MMAC1. Conversely, wild-type MMSC2 or the PDZ domain interacting with MMAC1 can be used in a protein binding assay or biochemical function assay to detect normal or mutant MMAC1 proteins, where the mutant proteins are proteins lacking a wild-type C-terminus.

A mutant MMSC2 gene or gene product or a mutant MMAC1 can also be detected in other human body samples, such as serum, stool, urine and sputum. The same techniques discussed above for detection of mutant genes or gene products in tissues can be applied to other body samples. By screening such body samples, a simple early diagnosis can be achieved for cancer resulting from a mutation in the MMSC2 gene.

The primer pairs of the present invention are useful for determination of the nucleotide sequence of a particular MMSC2 allele using PCR. The pairs of single-stranded DNA primers for MMSC2 can be annealed to sequences within or surrounding the MMSC2 gene in order to prime amplifying DNA synthesis of the gene itself. A complete set of these primers allows synthesis of all of the nucleotides of the gene coding sequences, i.e., the exons. The set of primers preferably allows synthesis of both intron and exon sequences. Allele-specific primers can also be used. Such primers anneal only to particular MMSC2 mutant alleles, and thus will only amplify a product in the presence of the mutant allele as a template.

In order to facilitate subsequent cloning of amplified sequences, primers may have restriction enzyme site sequences appended to their 5' ends. Alternatively, primers can also be prepared with 5' phosphoryl groups which will allow for blunt end coloning of amplied sequences. Thus, all nucleotides of the primers are derived from MMSC2 sequence or sequences adjacent to MMSC2, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of MMSC2, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the MMSC2 gene or mRNA using other techniques Mutations which interfere with the function of the MMSC2 gene product are involved in the pathogenesis of cancer. Thus, the presence of an altered (or a mutant) MMSC2 gene which produces a protein having a loss of function, or altered function, directly increases the risk of cancer. In order to detect a MMSC2 gene mutation, a biological sample is prepared and analyzed for a difference between the sequence of the allele being analyzed and the sequence of the wild-type allele. Mutant MMSC2 alleles can be initially identified by any of the techniques described above. The mutant alleles are then sequenced to identify the specific mutation of the particular mutant allele. Alternatively, mutant alleles can be initially identified by identifying mutant (altered) proteins, using conventional techniques. The mutant alleles are then sequenced to identify the specific mutation for each allele. The mutations, especially those which lead to an altered function of the protein, are then used for the diagnostic and prognostic methods of the present invention.

Definitions

The present invention employs the following definitions.

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, nucleic acid sequence based amplification (3SR or NASBA) and repair chain reaction (RCR). These methods are well known and widely practiced in the art. See, e.g., U.S. Pat. Nos. 4,683,195 and 4,683,202 and Innis et al., 1990 (for PCR); Wu et al., 1989a and EP 320,308A (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the MMSC2 region are preferably complementary to, and hybridize specifically to sequences in the MMSC2 region or in regions that flank a target region therein. MMSC2 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the MMSC2 polypeptide and fragments thereof or to polynucleotide sequences from the MMSC2 region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the MMSC2 polypeptide or fragment. Monoclonal antibodies may be made by injecting mice with the protein polypeptides, fusion proteins or fragments thereof. Monoclonal antibodies will be screened by ELISA and tested for specific immunoreactivity with MMSC2 polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et cal., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulills may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. In addition, as disclosed herein, MMAC1 and PDZ binding peptides, as well as several other proteins, bind to or interact with MMSC2. Each of these proteins are also considered binding partners herein. Further binding partners can be identifed using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"MMSC2 Allele" refers to normal alleles of the MMSC2 locus that interact with MMAC1 as well as alleles of MMSC2 carrying variations that affect the interaction with MMAC1 and that cause cancer.

"MMSC2 Locus", "MMSC2 Gene", "MMSC2 Nucleic Acids" or "MMSC2 Polynucleotide" each refer to polynucleotides, all of which are in the MMSC2 region, that are likely to be expressed in normal tissue, certain alleles of which adversely affect the interaction with MMAC1 and result in cancer. The MMSC2 locus is intended to include coding sequences, intervening sequences and regulatory elements controlling transcription and/or translation. The MMSC2 locus is intended to include all allelic variations of the DNA sequence.

These terms, when applied to a nucleic acid, refer to a nucleic acid which encodes a human MMSC2 polypeptide, fragment, homolog or variant, including, e.g., protein fusions or deletions. The nucleic acids of the present invention will possess a sequence which is either derived from, or substantially similar to a natural MMSC2-encoding gene or one having substantial homology with a natural MMSC2-encoding gene or a portion thereof.

The MMSC2 gene or nucleic acid includes normal alleles of the MMSC2 gene, both silent alleles having no effect on the amino acid sequence of the MMSC2 polypeptide and alleles leading to amino acid sequence variants of the MMSC2 polypeptide that do not substantially affect its function. These terms also include alleles having one or more mutations which adversely affect the function of the MMSC2 polypeptide. A mutation may be a change in the MMSC2 nucleic acid sequence which produces a deleterious change in the amino acid sequence of the MMSC2 polypeptide, resulting in partial or complete loss of MMSC2 function, or may be a change in the nucleic acid sequence which results in the loss of effective MMSC2 expression or the production of aberrant forms of the MMSC2 polypeptide.

The MMSC2 nucleic acid may be that shown in SEQ ID NO:2, or it may be an allele as described above, or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID NO:2 yet encode a polypeptide with the same amino acid sequence as shown in SEQ ID NO:3. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NO:3. Nucleic acid encoding a polypeptide which is an amino acid sequence variant, derivative or allele of the amino acid sequence shown in SEQ ID NO:3 is also provided by the present invention.

The MMSC2 gene also refers to (a) any DNA sequence that (i) hybridizes to the complement of the DNA sequences that encode the amino acid sequence set forth in SEQ ID NO:3 under highly stringent conditions (Ausubel et al.) (ii) and encodes a gene product functionally equivalent to MMSC2, or (b) any DNA sequence that (i) hybridizes to the complement of the DNA sequences that encode the amino acid sequence set forth in SEQ ID NO:3 under less stringent conditions, such as moderately stringent conditions (Ausubel et al.), and (ii) encodes a gene product functionally equivalent to MMSC2. The invention also includes nucleic acid molecules that are the complements of the sequences described herein.

The polynuclcotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the MMSC2 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, RNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a MMSC2-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega, U. S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the MMSC2 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these values (e.g., 9, 10, 11, 16, 23, 30, 38, 50, 72, 121, etc, nucleotides), or nucleic acids having more than 500 nucleotides, or any number of nucleotides between 500 and the number shown in SEQ ID NO:2. The present invention includes all novel nucleic acids having at least 8 nucleotides derived from SEQ ID NO:2, its complement or functionally equivalent nucleic acid sequences. The present invention does not include nucleic acids which exist in the prior art. That is, the present invention includes all nucleic acids having at least 8 nucleotides derived from SEQ ID NO:2 with the proviso that it does not include nucleic acids existing in the prior art.

"MMSC2 protein" or "MMSC2 polypeptide" refers to a protein or polypeptide encoded by the MAIMSC2 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native MMSC2 sequence, preferably in excess of about 90%, and more preferably at least about 95% homologous. Also included are proteins encoded by DNA which hybridize under high or low stringency conditions, to MMSC2-encoding nucleic acids and closely related polypeptides or proteins retrieved by antisera to the MMSC2 protein(s).

The MMSC2 polypeptide may be that shown in SEQ ID NO:3 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the MMSC2 polypeptide. Such polypeptides may have an amino acid sequence which differs from that set forth in SEQ ID NO:3 by one or more of addition, substitution, deletion or insertion of one or more amino acids. Preferred such polypeptides have MMSC2 function.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the MMSC2 polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydrophathic index of amino acids may be considered. The importance of the hydrophobic amino acid index in conferring interactive biological function on a protein is generally understood in the art (Kyte & Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended mainer. For instance, a promoter is operably linked to a coding sequence if the promoter affects its transcription or expression.

The term "peptide mimetic" or "mimetic" is intended to refer to a substance which has the essential biological activity of the MMSC2 polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural MMSC2 polypeptide.

"Probes". Polynucleotide polymorphisms associated with MMSC2 alleles which predispose to cancer are detected by hybridization with a polynucleotide probe which forms a stable hybrid with that of the target sequence, under highly stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of a MMSC2 susceptibility allele.

Probes for MMSC2 alleles may be derived from the sequences of the MMSC2 region, its cDNA, functionally equivalent sequences, or the complements thereof. The probes may be of any suitable length, which span all or a portion of the MMSC2 region, and which allow specific hybridization to the region. If the target sequence contains a sequence identical to that of the probe, the probes may be short, e.g., in the range of about 8–30 base pairs, since the hybrid will be relatively stable under even highly stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding MMSC2 are preferred as probes. This definition therefore includes probes of sizes 8 nucleotides through 9000 nucleotides. Thus, this definition includes probes of 8, 12, 15, 20, 25, 40, 60, 80, 100, 200, 300, 400, 500 nucleotides, or probes having any number of nucleotides within these values (e.g., 9, 10, 11, 16, 23, 30, 38, 50, 72, 121, etc, nucleotides), or probes having more than 500 nucleotides, or any number of nucleotides between 500 and the number shown in SEQ ID NO:2. The probes may also be used to determine whether mRNA encoding MMSC2 is present in a cell or tissue. The present invention includes all novel probes having at least 8 nucleotides derived from SEQ ID NO:2, its complement or functionally equivalent nucleic acid sequences. The present invention does not include probes which exist in the prior art. That is, the present invention includes all probes having at least 8 nucleotides derived from SEQ ID NO:2 with the proviso that it does not include probes existing in the prior art.

Similar considerations and nucleotide lengths are also applicable to primers which may be used for the amplification of all or part of the MMSC2 gene. Thus, a definition for primers includes primers of 8, 12, 15, 20, 25, 40, 60, 80, 100, 200, 300, 400, 500 nucleotides, or primers having any number of nucleotides within these values (e.g., 9, 10, 11, 16, 23, 30, 38, 50, 72, 121, etc, nucleotides), or primers having more than 500 nucleotides, or any number of nucleotides between 500 and 9000. The primers may also be used to determine whether mRNA encoding MMSC2 is present in a cell or tissue. The present invention includes all novel primers having at least 8 nucleotides derived from the MMSC2 locus for amplifying the MMSC2 gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for MMSC2 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of MMSC2 polypeptides. Immunological activities include both immunogenic function in a target immune system, as well as sharing of immunological epitopes for binding, serving as either a competitor or substitute antigen for an epitope of the MMSC2 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for MMSC2 polypeptides or fragments thereof is described below.

The present invention also provides for fusion polypeptides, comprising MMSC2 polypeptides and fragments. Homologous polypeptides may be fusions between two or more MMSC2 polypeptide sequences or between the sequences of MMSC2 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, α-amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides arc described, for example, in Merrifield, 1963.

"Protein purification" refers to various methods for the isolation of the MMSC2 polypeptides from other biological material, such as from cells transformed with recombinant nucleic acids encoding MMSC2, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A MMSC2 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measure of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type MMSC2 nucleic acid or wild-type MMSC2 polypeptide. The modified polypeptide will be substantially homologous to the wild-type MMSC2 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type MMSC2 polypeptide. Alternatively, the similarity of function (activity) of the modified polypeptide may be higher than the activity of the wild-type MMSC2 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type MMSC2 gene function produces the modified protein described above.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

Preparation of Recombinant or Chemically Synthesized Nucleic Acids; Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian, plant, insect or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage and Carruthers, 1981 or the triester method according to Matteucci and Caruthers, 1981, and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook et al., 1989 or Ausubel et al., 1992.

An appropriate promoter and other necessary vector sequences will be selected so as to be functional in the host, and may include, when appropriate, those naturally associated with the MMSC2 gene. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrbgenase, enzymes responsible for maltose and galactose utilization, and others. Vectors and promoters suitable for use in yeast expression are further described in Hitzeman et al. (EP 73,675A). Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). See also, e.g., U.S. Pat. No. 5,691,198.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above and in U.S. Pat. No. 5,691,198, will be referred to herein as "transformation." The cells into which have been introduced nucleic acids described above are meant to also include the progeny of such cells.

Large quantities of the nucleic acids and polypeptides of the present invention may be prepared by expressing the MMSC2 nucleic acid or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), 1979. Examples of commonly used mammalian host cell lines are VERO and HeLa cells, Chinese hamster ovary (CHO) cells, and WI38, BHK, and COS cell lines. An example of a commonly used insect cell line is SF9. However, it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of MMSC2 polypeptide.

The probes and primers based on the MMSC2 gene sequence disclosed herein are used to identify homologous MMSC2 gene sequences and proteins in other species. These gene sequences and proteins are used in the diagnostic/prognostic, therapeutic and drug screening methods described herein for the species from which they have been isolated.

Methods of Use: Drug Screening

This invention is particularly useful for screening compounds by using the MMSC2 polypeptide or binding fragment thereof in any of a variety of drug screening techniques, such as those described herein and in published PCT application WO 97/02048. Since MMSC2 acts as a scaffold that binds to MMAC 1, the phosphatase substrate(s) and the (probably oncogene) tyrosine kinase(s), a valuable drug candidate will be a drug that can prevent binding of either the substrate(s) or the tyrosine kinase(s) to MMSC2.

The MMSC2 polypeptide or fragment employed in such a test may either be free in solution, affixed to a solid support, or borne on a cell surface. One method of drug screening utilizes eukaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a MMSC2 polypeptide or fragment and the agent being tested, or examine the degree to which the formation of a complex between a MMSC2 polypeptide or fragment and a known ligand, e.g., MMAC1, is aided or interfered with by the agent being tested.

Thus, the present invention provides methods of screening for drugs comprising contacting such an agent with a MMSC2 polypeptide or fragment thereof and assaying (i) for the presence of a complex between the agent and the MMSC2 polypeptide or fragment, or (ii) for the presence of a complex between the MMSC2 polypeptide or fragment and a ligand, by methods well known in the art. In such competitive binding assays the MMSC2 polypeptide or fragment is typically labeled. Free MMSC2 polypeptide or fragment is separated from that present in a protein:protein complex, and the amount of free (i.e., uncomplexed) label is a measure of the binding of the agent being tested to MMSC2 or its interference with or promotion of MMSC2:ligand binding, respectively. One may also measure the amount of bound, rather than free, MMSC2. It is also possible to label the ligand rather than the MMSC2 and to measure the amount of ligand binding to MMSC2 in the presence and in the absence of the drug being tested.

Another technique for drug screening provides high throughput screening for compounds having suitable binding affinity to the MMSC2 polypeptides and is described in detail in Geysen (published PCT application WO 84/03564). Briefly stated, large numbers of different small peptide test compounds are synthesized on a solid substrate, such as plastic pins or some other surface. The peptide test compounds are reacted with MMSC2 polypeptide and washed. Bound MMSC2 polypeptide is then detected by methods well known in the art.

Purified MMSC2 can be coated directly onto plates for use in the aforementioned drug screening techniques. However, non-neutralizing antibodies to the polypeptide can be used to capture antibodies to immobilize the MMSC2 polypeptide on the solid phase.

This invention also contemplates the use of competitive drug screening assays in which neutralizing antibodies capable of specifically binding the MMSC2 polypeptide compete with a test compound for binding to the MMSC2 polypeptide or fragments thereof. In this manner, the antibodies can be used to detect the presence of any peptide which shares one or more antigenic determinants of the MMSC2 polypeptide.

The above screening methods are not limited to assays employing only MMSC2 but are also applicable to studying MMSC2-protein complexes, e.g., the complex which occurs between MMSC2 and MMAC1. The effect of drugs on the activity of this complex, especially when either the MMSC2 or the MMSC2 binding protein (e.g., MMAC1) contains a mutation, is analyzed.

In accordance with these methods, the following assays are examples of assays which can be used for screening for drug candidates.

A mutant MMSC2 (per se or as part of a fusion protein) is mixed with a wild-type protein (per se or as part of a fusion protein) to which wild-type MMSC2 binds. This mixing is performed in both the presence of a drug and the absence of the drug, and the amount of binding of the mutant MMSC2 with the wild-type protein is measured. If the amount of the binding is more in the presence of said drug than in the absence of said drug, the drug is a drug candidate for treating cancer resulting from a mutation in MMSC2. This assay is useful where the wild-type protein is a tumor suppressor, such as MMAC1.

A wild-type MMSC2 (per se or as part of a fusion protein) is mixed with a wild-type protein (per se or as part of a fusion protein) to which wild-type MMSC2 binds. This mixing is performed in both the presence of a drug and the absence of the drug, and the amount of binding of the wild-type MMSC2 with the wild-type protein is measured. If the amount of the binding is more in the presence of said drug than in the absence of said drug, the drug is a drug candidate for treating cancer resulting from a mutation in MMSC2. This assay is useful where the wild-type protein is a tumor suppressor, such as MMAC1.

A mutant MMSC2 (per se or as part of a fusion protein) is mixed with a wild-type protein (per se or as part of a fusion protein) to which wild-type MMSC2 binds. This mixing is performed in both the presence of a drug and the absence of the drug, and the amount of binding of the mutant MMSC2 with the wild-type protein is measured. If the amount of the binding is less in the presence of said drug than in the absence of said drug, the drug is a drug candidate for treating cancer resulting from a mutation in MMSC2. This assay is useful if the protein is an oncoprotein or a substrate of the oncoprotein.

A wild-type MMSC2 (per se or as part of a fusion protein) is mixed with a wild-type protein (per se or as part of a fusion protein) to which wild-type MMSC2 binds. This mixing is performed in both the presence of a drug and the absence of the drug, and the amount of binding of the wild-type MMSC2 with the wild-type protein is measured. If the amount of the binding is less in the presence of said drug than in the absence of said drug, the drug is a drug candidate for treating cancer resulting from a mutation in MMSC2 or a cancer resulting from a mutation in MMAC1. This assay is useful if the protein is an oncoprotein or a substrate of the oncoprotein.

A mutant protein, which as a wild-type protein binds to MMSC2 (per se or as part of a fusion protein) is mixed with a wild-type MMSC2 (per se or as part of a fusion protein). This mixing is performed in both the presence of a drug and the absence of the drug, and the amount of binding of the mutant protein with the wild-type MMSC2 is measured. If the amount of the binding is less in the presence of said drug than in the absence of said drug, the drug is a drug candidate for treating cancer resulting from a mutation in the gene encoding the protein.

The polypeptide of the invention may also be used for screening compounds developed as a result of combinatorial library technology. Combinatorial library technology provides an efficient way of testing a potential vast number of different substances for ability to modulate activity of a polypeptide. Such libraries and their use are known in the art. The use of peptide libraries is preferred. See, for example, WO 97/02048.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993). This system may be used as a coarse screen prior to testing a substance for actual ability to modulate activity of the polypeptide. Alternatively, the screen could be used to screen test substances for binding to a MMSC2 specific binding partner, such as MMAC1, or to find mimetics of the MMSC2 polypeptide.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordancewith what is disclosed herein, but also a pharmaceutical composition, medicament, drug or other composition comprising such a substance, a method comprising administration of such a composition comprising such a substance, a method comprising administration of such a composition to a patient, e.g., for treatment (which may include preventative treatment) of cancer, use of such a substance in the manufacture of a composition for administration, e.g., for treatment of cancer, and a method of making a pharmaceutical composition comprising admixing such a substance with a pharmaceutically acceptable excipient, vehicle or carrier, and optionally other ingredients. A substance identified using as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the mino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Nucleic Acid Diagnosis and Diagnostic Kits

In order to detect the presence of a MMSC2 allele predisposing an individual to cancer, a biological sample such as blood is prepared and analyzed for the presence or absence of susceptibility alleles of MMSC2. In order to detect the presence of cancer or as a prognostic indicator, a biological sample is prepared and analyzed for the presence or absence of mutant alleles of MMSC2. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant MMSC2 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired, to extract the nucleic acids. The sample nucleic acid may be prepared in various ways to facilitate detection of the target sequence, e.g., denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region for MMSC2. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences. Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; U.S. Pat. No. 4,868,105; and in EP 225,807A.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes, see Jablonski et al., 1986.

Two-step label amplification methodologies are known in the art. These assays work on the principle that a small ligand (such as digoxigenin, biotin, or the like) is attached to a nucleic acid probe capable of specifically binding MMSC2. Allele specific probes are also contemplated within the scope of this example and exemplary allele specific probes include probes encompassing the predisposing mutations of this disclosure.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting MMSC2. Thus, in one example to detect the presence of MMSC2 in a cell sample, more than one probe complementary to the gene is employed and in particular the number of different probes is alternatively two, three, or five different nucleic acid probe sequences. In another example, to detect the presence of mutations in the MMSC2 gene sequence in a patient, more than one probe complementary to these genes is employed where the cocktail includes probes capable of binding to the allele-specific mutations identified in populations of patients with alterations in MMSC2. In this embodiment, any number of probes can be used, and will preferably include probes corresponding to the major gene mutations identified as predisposing an individual to cancer.

Methods of Use: Peptide Diagnosis and Diagnostic Kits

The presence of cancer can also be detected on the basis of the alteration of wild-type MMSC2 polypeptide. Such alterations can be determined by sequence analysis in accordance with conventional techniques. More preferably, antibodies (polyclonal or monoclonal) are used to detect differences in, or the absence of MMSC2 peptides. Techniques for raising and purifying antibodies are well known in the art and any such techniques may be chosen to achieve the preparations claimed in this invention. In a preferred embodiment of the invention, antibodies will immunoprecipitate MMSC2 proteins from solution as well as react with these proteins on Western or immunoblots of polyacrylamide gels. In another preferred embodiment, antibodies will detect MMSC2 proteins in paraffin or frozen tissue sections, using immunocytochemical techniques.

Preferred embodiments relating to methods for detecting MMSC2 or its mutations include enzyme linked immunosorbent assays (ELISA), radioimmunoassays (RIA), immunoradiometric assays (IRMA) and immunoenzymatic assays (IEMA), including sandwich assays using monoclonal and/ or polyclonal antibodies. Exemplary sandwich assays are described by David et al., in U.S. Pat. Nos. 4,376,110 and 4,486,530, hereby incorporated by reference.

Alternatively, alterations in the MMSC2 sequence can be determined by detecting alterations in the interaction of MMSC2 with MMAC1 or the C-terminus of MMAC1. Wild-type MMAC1 or its C-terminus can be bound to a solid phase and the interaction with MMSC2 assayed by conventional techniques. Analogously, alterations in MMAC1 which affect its interaction with MMSC2 can be detected using wild-type MMSC2 or its PDZ domain which interacts with MMAC1 bound to a solid phase.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., MMSC2 polypeptide) by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., MMSC2 polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved MMSC2 polypeptide activity or stability or which act as inhibitors, agonists, antagonists, etc. of MMSC2 polypeptide activity. By virtue of the availability of cloned MMSC2 sequence, sufficient amounts of the MMSC2 polypeptide may be made available to perform such analytical studies as x-ray crystallography. In addition, the knowledge of the MMSC2 protein sequence provided herein will guide those employing computer modeling techniques in place of, or in addition to x-ray crystallography.

Methods of Use: Gene Therapy

According to the present invention, a method is also provided of supplying wild-type MMSC2 function to a cell which carries a mutant MMSC2 allele. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner.

As generally discussed above, the MMSC2 gene or fragment, where applicable, may be employed in gene therapy methods in order to increase the amount of the expression products of such gene in cells. It may also be useful to increase the level of expression of the MMSC2 gene even in those persons in which the mutant gene is expressed at a "normal" level, but the gene product is not fully functional.

Gene therapy would be carried out according to generally accepted methods, for example, as described by Friedman (1991) or Culver (1996). Cells from a patient would be first analyzed by the diagnostic methods described above, to ascertain the production of MMSC2 polypeptide in the cells. A virus or plasmid vector (see further details below), containing a copy of the MMSC2 gene linked to expression control elements, is prepared. The vector may be capable of replicating inside the cells. Alternatively, the vector may be replication deficient and is replicated in helper cells for use in gene therapy. Suitable vectors are known, such as disclosed in U.S. Pat. No. 5,252,479, published PCT application WO 93/07282 and U.S. Pat. No. 5,691,198. The vector is then injected into the patient. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors or as the basis for preparing gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990; Schneider et al., 1998), vaccinia virus (Moss, 1992), adeno-associated virus (Muzyczka, 1992; Ohi et al., 1990;

Russell & Hirata, 1998), herpesviruses including HSV and EBV (Margolskee, 1992; Johnson et al., 1992; Fink et al., 1992; Breakfield and Geller, 1987; Freese et al., 1990; Fink et al., 1996), lentiviruses (Naldini et al., 1996), vaccinia virus (Moss, 1996), Sindbis and Semliki Forest virus (Berglund et al., 1993), and retroviruses of avian (Brandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Constantini and Lacy, 1981); membrane fusion-mediated transfer via liposomes (Feigner et al., 1987; Wang and Huang, 1989; Kaneda et al., 1989; Stewart et al., 1992; Nabel et al., 1990; Lim et al., 1992); and direct DNA uptake and receptor-mediated DNA transfer (Wolff et al., 1990; Wu et al., 1991; Zenke et al., 1990; Wu et al., 1989 b; Wolff et al., 1991; Wagner et al., 1990; Wagner et al., 1991; Cotten et al., 1990; Curiel et al., 1991a; Curiel et al., 1991b).

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors Schneider et al. (1998) and U.S. Pat. No. 5,691,198.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes MMSC2, expression will produce MMSC2. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to brain tissue is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy is as follows: patients who carry a MMSC2 susceptibility allele are treated with a gene delivery vehicle such that some or all of their brain precursor cells receive at least one additional copy of a functional normal MMSC2 allele, respectively. In this step, the treated individuals have reduced risk of cancer to the extent that the effect of the susceptible allele has been countered by the presence of the normal allele.

Methods of Use: Peptide Therapy

Peptides which have MMSC2 activity can be supplied to cells which carry a mutant or missing MMSC2 allele. Protein can be produced by expression of the cDNA sequence in bacteria, for example, using known expression vectors. Alternatively, MMSC2 polypeptide can be extracted from MMSC2-producing mammalian cells. In addition, the techniques of synthetic chemistry can be employed to synthesize MMSC2 protein. Any of such techniques can provide the preparation of the present invention which comprises the MMSC2 protein. The preparation is substantially free of other human proteins. This is most readily accomplished by synthesis in a microorganism or in vitro.

Active MMSC2 molecules can be introduced into cells by microinjection or by use of liposomes, for example. Alternatively, some active molecules may be taken up by cells, actively or by diffusion. Supply of molecules with MMSC2 activity should lead to inhibition of cancer. Other molecules with MMSC2 activity (for example, peptides, drugs or organic compounds) may also be used to effect such an inhibition. Modified polypeptides having substantially similar function are also used for peptide therapy.

Methods of Use: Transformed Hosts

Animals for testing therapeutic agents can be selected after mutagenesis of whole animals or after treatment of germline cells or zygotes. Such treatments include insertion of mutant MMSC2 alleles, usually from a second animal species, as well as insertion of disrupted homologous genes. Alternatively, the endogenous MMSC2 gene of the animals may be disrupted by insertion or deletion mutation or other genetic alterations using conventional techniques (Capecchi, 1989; Valancius and Smithies, 1991; Hasty el al., 1991; Shinkai et al., 1992; Mombaerts et al., 1992; Philpott et al., 1992; Snouwaert et al., 1992; Donehower et al., 1992). After test substances have been administered to the animals, the presence of cancer must be assessed. If the test substance prevents or suppresses the appearance of cancer, then the test substance is a candidate therapeutic agent for treatment of cancer. These animal models provide an extremely important testing vehicle for potential therapeutic products.

Methods of Use: Transgenic/Knockout Animals and Models

In one embodiment of the invention, transgenic animals are produced which contain a functional transgene encoding a functional MMSC2 polypeptide or variants thereof. Transgenic animals expressing MMSC2 transgenes, recombinant cell lines derived from such animals and transgenic embryos may be useful in methods for screening for and identifying agents that induce or repress function of MMSC2. Transgenic animals of the present invention also can be used as models for studying indications such as cancers.

In one embodiment of the invention, a MMSC2 transgene is introduced into a non-human host to produce a transgenic animal expressing a human or murine MMSC2 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous MMSC2 by homologous recombination between the transgene and the endogenous gene; or the endogenous gene may be eliminated by deletion as in the preparation of "knock-out" animals. Typically, a MMSC2 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress MMSC2 or express a mutant form of the polypeptide. Alternatively, the absence of a MMSC2 in "knock-out" mice permits the study of the effects that loss of MMSC2 protein has on a cell in vivo. Knock-out mice also provide a model for the development of MMSC2-related cancers.

Methods for producing knockout animals are generally described by Shastry (1995, 1998) and Osterrieder and Wolf (1998). The production of conditional knockout animals, in which the gene is active until knocked out at the desired time is generally described by Feil et al. (1996), Gagneten et al. (1997) and Lobe and Nagy (1998). Each of these references is incorporated herein by reference.

As noted above, transgenic animals and cell lines derived from such animals may find use in certain testing experiments. In this regard, transgenic animals and cell lines capable of expressing wild-type or mutant MMSC2 may be exposed to test substances. These test substances can be screened for the ability to enhance wild-type MMSC2 expression and or function or impair the expression or function of mutant MMSC2.

Pharmaceutical Compositions and Routes of Administration

The MMSC2 polypeptides, antibodies, peptides and nucleic acids of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or spealists, and typically takes account of the disorder to be treated, the condition of the individual patient, the site of delivery, the method of administration and other factors known to practitioners. Examples of techniques and protocols can be found in *Remington's Parmaceutical Sciences*.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635. designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

The identification of the association between the MMSC2 gene mutations and cancer permits the early presymptomatic screening of individuals to identify those at risk for developing cancer. To identify such individuals, MMSC2 alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal MMSC2 gene or appropriate fragment (coding sequence or genomic sequence) are determined and then compared, or (2) the RNA transcripts of the MMSC2 gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the MMSC2 gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal MMSC2 gene.

Alternatively, polymerase chain reactions (PCRs) are performed with primer pairs for the 5' region or the exons of the MMSC2 gene. PCRs can also be performed with primer pairs based on any sequence of the normal MMSC2 gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common MMSC2 gene variants by amplifying the individual's DNA using suitable primer pairs and analyzing the amplified product, e.g., by dot-blot hybridization using allele-specific oligonucleotide probes.

The second method employs RNase A to assist in the detection of differences between the normal MMSC2 gene and defective genes. This comparison is performed in steps using small (~500 bp) restriction fragments of the MMSC2 gene as the probe. First, the MMSC2 gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65).

The SP6-based plasmids containing inserts of the MMSC2 gene fragments are transcribed in vitro using the SP6 transcription system, well known in the art, in the presence of [$\alpha$-$^{32}$P]GTP, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the MMSC2 fragment and the MMSC2 allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the MMSC2 gene and the consequent presence of cancer. These variants can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk for cancer at, or even before, birth. Finally, this invention changes our understanding of the cause and treatment of cancer.

EXAMPLES

The present invention is further detailed in the following Examples, which are offered by way of illustration and are not intended to limit the invention in any manner. Standard techniques well known in the art or the techniques specifically described below are utilized.

Example 1

Identification of MMSC2

A yeast two-hybrid assay was performed using conventional techniques, such as described by Fields and Song (1989), Chevray and Nathans (1992), Bartel et al. (1993) and Lee et al. (1995). Sequence encoding the C-terminal 15 amino acids of MMAC1 (NEPFDEDQHTQITKV; SEQ ID NO:4) plus its stop codon was generated using an oligonucleotide synthesizer and was ligated to plasmid pGBT.C such that the coding sequence of MMAC1 was in-frame with coding sequence for the Gal4p DNA-binding domain. This plasmid construct was introduced into the yeast reporter strain J692 along with a library of activation domain fusion plasmids prepared from human kidney cDNA (Clontech). Transformants were spread onto 20–150 mm plates of yeast minimal media lacking leucine, tryptophan, and histidine, and containing 25 mM 3-amino-1,2,4-triazole (Gietz et al., 1995; Bartel and Fields, 1995). After one week incubation at 30° C., yeast colonies were assayed for expression of the lacZ reporter gene by beta-galactosidase filter assay (Breeden and Naysmyth, 1985). Colonies that both grew in the absence of histidine and were positive for production of beta-galactosidase were chosen for further characterization.

The activation domain plasmid was purified from positive colonies by the smash-and-grab technique. These plasmids were introduced into *E. coli* DH 10B (Gibco BRL) by electroporation and purified from *E. coli* by the alkaline lysis method. To test for the specificity of the interaction, specific activation domain plasmids were cotransformed into strain J692 with plasmids encoding various DNA-binding domain fusion proteins, including fusions to C-terminal segments of MMAC1 and human lamin C. Transformants from these experiments were assayed for expression of the HIS3 and lcZ reporter genes. Positives that expressed reporter genes with MMAC1 constructs and not with lamin C constructs encode bona fide MMAC1-interacting proteins. These proteins were identified and characterized by sequence analysis of the insert of the appropriate activation domain plasmid.

Five of the clones encoding bona fide MMAC1-interacting proteins were named PDZBN2B, PDZBN3A, PDZBN5B, PDZBN18D, and pdzk4. Comparison of the sequences of these clones suggested that they were all partial cDNAs derived from the same novel gene. A search of GenBank with these sequences revealed strong sequence similarity with a partial mouse cDNA sequence called 9ORF binding protein 1 (9BP-1)(GenBank Accession #AF000168).

Several rounds of cDNA library screening were required to identify eDNA clones that could be assembled into the full length MMSC2 sequence. In the first round, a 509 base pair(bp) probe was developed from the 5' end of clone PDZBN2B using primers 9BP-1 F1: AGACAGCAAAGATGACAGTAA (SEQ ID NO:5) and

9BP-1 R4: CTTCCTCCTCTTTGTATGGG (SEQ ID NO:6).

This probe was used to screen a human placental cDNA library and a human prostate cDNA library. Two of the informative clones obtained were p118a(placental) and pr63 (prostate). A search of GenBank with this additional sequence yielded an additional human EST (GenBank Accesion #C75629). For the second round of cDNA library screening, a 202 bp probe was developed from the 5' end of this EST using primers 9BP1 #2: GCTTTTGCCGAAATGGGTAGT (SEQ ID NO:7) and

9BP1 #2: GATCGGTCTTTGTTCCCAGCA (SEQ ID NO:8).

This probe was used to screen a human prostate cDNA library; two of the informative clones obtained were clone #10 and clone #3. For the third round of cDNA library screening, a 172 bp probe was developed from the 5' end of clone #3 using primers 9BP-1 #5: TGTGAGCAAGTTTAGTGAG (SEQ ID NO:9) and

9BP-1 #7: GGTGATTTTCCCCAAGTAA (SEQ ID NO: 10)

and used to screen a human prostate cDNA library. One of the resulting clones, clone #6, yeiled the start codon and and part of the 5' UTR, including in-frame upstream stop codons. The nucleotide sequence for MMSC2 is set forth in SEQ ID NO:2 with the amino acid sequence of the encoded protein set forth in SEQ ID NO:3.

Figure 2:
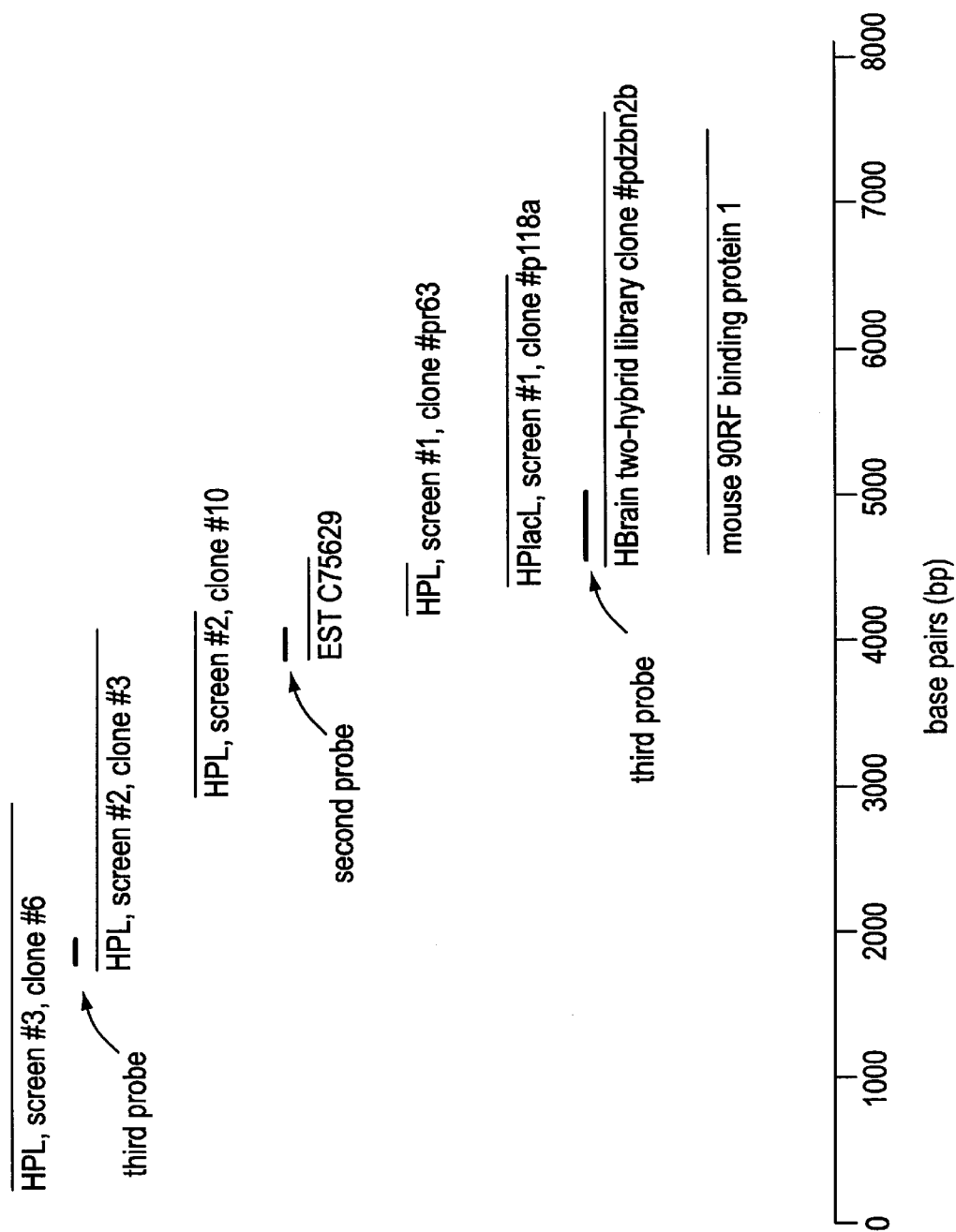
FIG. 2 shows a diagram of the key clones used to assemble the full length MMSC2 sequence, the probes used to identify those clones, and the relative position of the partially sequenced mouse ortholog 9BP-1(GenBank Accession #AF000168).

FIG. 1 shows a diagram of MMSC2 indicating the position of ORF and the positions of the 13 PDZ domains. FIG. 2 shows a diagram of the key clones used to assemble the full length MMSC2 sequence, the probes used to identify those clones, and the relative position of the partially sequenced mouse ortholog 9BP-1(Accession #AF000168). Within the 5' UTR, the in-frame upstream stop codon at nucleotide 42 demonstrates that the start codon at nucleotide 57 has been correctly indentified. The 13 PDZ domains correspond to the amino acids of MMSC2 as shown in Table 1.

TABLE 1

Sequence Correspondence of 13 PDZ Domains

| Domain Number | Domain Name | Amino Acid Span |
| --- | --- | --- |
| 1 | P15 | 136–222 |
| 2 | P14 | 256–335 |
| 3 | P13 | 376–461 |
| 4 | P10 | 555–632 |
| 5 | P12 | 699–785 |
| 6 | P11 | 1007–1090 |
| 7 | P9 | 1150–1241 |
| 8 | P8 | 1316–1398 |
| 9 | P7 | 1439–1529 |
| 10 | P1 | 1595–1677 |
| 11 | P2 | 1691–1772 |
| 12 | P3 | 1828–1913 |
| 13 | P4 | 1953–2037 |

Example 2

Identification of MMSC2-interacting Proteins by Two-hybrid Analysis

DNA fragments encoding all or portions of MMSC2 are ligated to a two-hybrid DNA-binding domain vector such as pGBT.C such that the coding sequence of MMSC2 is in-frame with coding sequence for the Gal4p DNA-binding domain. These DNA fragments may encode specific PDZ domains of MMSC2 plus the 5 to 10 amino acids N- and C-terminal of each specific PDZ. A plasmid that encodes a DNA-binding domain fusion to a fragment of MMSC2 PDZ is introduced into the yeast reporter strain (such as J692) along with a library of cDNAs fused to an activation domain. Transformants are spread onto 20–150 mm plates of selective media, such as yeast minimal media lacking leucine, tryptophan, and histidine, and containing 25 mM 3-amino-1,2,4-triazole. After one week incubation at 30° C., yeast colonies are assayed for expression of the lacZ reporter gene by beta-galactosidase filter assay. Colonies that both grow in the absence of histidine and are positive for production of beta-galactosidase are chosen for further characterization.

The activation domain plasmid is purified from positive colonies by the smash-and-grab technique. These plasmids are introduced into *E. coli* (e.g., DH10B (Gibco BRL)) by electroporation and purified from *E. coli* by the alkaline lysis method. To test for the specificity of the interaction, specific activation domain plasmids are cotransformed into strain J692 with plasmids encoding various DNA-binding domain fusion proteins, including fusions to segments of MMSC2 and human lamin C. Transformants from these experiments are assayed for expression of the HIS3 and lacZ reporter genes. Positives that express reporter genes with MMSC2 constructs and not with larnin C constructs encode bona fide MMSC2-interacting proteins. These proteins are identified and characterized by sequence analysis of the insert of the appropriate activation domain plasmid.

Example 3

Characterization of the Binding Specificity of MMSC2 PDZ Domains by Two-Hybrid Analysis DNA fragments encoding specific PDZ domains of MMSC2 plus the 5 to 10 amino acids N- and C-terminal of each specific PDZ domain are generated by PCR amplification. These fragments are ligated to a two-hybrid DNA-binding domain vector such as pGBT.C such that the coding sequence of MMSC2 is in-frame with coding sequence for the Gal4p DNA-binding domain. An activation domain library is prepared that encodes an activation domain fused in-frame to random peptide sequences that end with a stop codon. An example of this type of library is the Clontech random peptide library. A plasmid that encodes a DNA-binding domain fusion to a specific MMSC2 PDZ domain is introduced into the yeast reporter strain (such as J692) along with a library of random peptides fused to an activation domain. Transformants are spread onto 20–150 mm plates of selective media, such as yeast minimal media lacking leucine, tryptophan, and histidine, and containing 25 mM 3-amino-1,2,4-triazole. After one week incubation at 30° C., yeast colonies are assayed for expression of the lacZ reporter gene by beta-galactosidase filter assay. Colonies that both grow in the absence of histidine and are positive for production of beta-galactosidase are chosen for sequence analysis. The insert of the activation domain construct is characterized by sequence analysis. The sequence of the peptide that binds to the MMSC2 PDZ domain is obtained by conceptual translation of the nucleotide sequence. Peptide sequences from multiple isolates are aligned to determine a consensus binding motif. This motif can be used to identify cellular proteins that bind MMSC2 and to develop small molecules that inhibit binding to these specific PDZ domains.

Example 4

In vitro Protein-Protein Interaction Assay cDNAs encoding each of the MMSC2 PDZ domains (amino acid residues identified in Table 1), and any desired control proteins, were generated by PCR and subcloned as glutathione S-transferase (GST) fusions in pGEX vectors (Pharmacia). After sequencing to confirm expression construct integrity, the resulting clones were expressed in E. coli and the desired fusion proteins isolated with glutathione-agarose and recovered with glutathione elution. These fusion proteins or control proteins were then adsorbed to different wells of a 96-well ELISA plate and remaining sites blocked with BSA. Synthetic commercially synthesized peptides encoding the desired PDZ-binding domain (i.e., the 16 C-terminal amino acids of MMAC1, or the C-terminal peptide sequences of interacting proteins identified by the approach of Example or the C-terminal peptide sequences identified by the approach of Example 3), or a control peptide, and biotinylated at the amino-terminus, were pre-bound to streptavidin-alkaline phosphatase in a 4:1 molar ratio. The biotinylated peptide streptavidin-alkaline phosphatase complexes were then blocked with free biotin. These pre- bound peptide streptavidin-alkaline phosphatase complexes were then incubated with the immobilized PDZ domains in wash buffer containing PBS, BSA and triton-X100. Unbound material was removed with repeated washes. Bound peptide/streptavidin-alkaline phosphatase complex was then quantitated by a calorimetric phosphatase assay read on a 96-well plate reader. The following peptides were used in the initial study:

SH3 binding peptide: biotin-SGSGILAPPVPPRNTR-COOH (SEQ ID NO:11)

MMAC1.388-403: biotin-ENEPFDEDQHTQITKV-COOH (SEQ ID NO:12).

The relative affinity of each of the 13 PDZ domains encoded by MMSC2 for an MMAC1 C-terminal PDZ peptide as measured by an ELISA assay is set forth in Table 2.

TABLE 2

PDZ Binding Assay

| Domain Number | Domain Name | Peptide | A405 |
|---|---|---|---|
| 1 | P15 | MMAC1 | 0.011 |
| | | SH3 | 0.007 |
| 2 | P14 | MMAC1 | 0.001 |
| | | SH3 | 0.006 |
| 3 | P13 | MMAC1 | 0.006 |
| | | SH3 | 0.008 |
| 4 | P10 | MMAC1 | 0.024 |
| | | SH3 | 0.010 |
| 5 | P12 | MMAC1 | 0.000 |
| | | SH3 | 0.005 |
| 6 | P11 | MMAC1 | 0.016 |
| | | SH3 | 0.017 |
| 7 | P9 | MMAC1 | 0.667 |
| | | SH3 | 0.006 |
| 8 | P8 | MMAC1 | 0.006 |
| | | SH3 | 0.008 |
| 9 | P7 | MMAC1 | 0.017 |
| | | SH3 | 0.009 |
| 10 | P1 | MMAC1 | 0.174 |
| | | SH3 | 0.002 |
| 11 | P2 | MMAC1 | 0.012 |
| | | SH3 | 0.009 |
| 12 | P3 | MMAC1 | 0.003 |
| | | SH3 | 0.011 |
| 13 | P4 | MMAC1 | 0.456 |
| | | SH3 | 0.006 |

The GST-affinity pull down assay is a complementary in vitro method for investigating protein-protein interactions. PDZ domain-GST fusion proteins are incubated with synthetic biotinylated peptides in wash buffer (these peptides were described above). Streptavidin magnetic beads are then added to recover the biotinylated peptide, then unbound material removed by washing. The beads are then incubated with SDS/DTT loading buffer at 100° C. and bound protein detected by SDS/PAGE and coomasie blue staining.

Example 5

Mutation Screening of MMSC2

Nested PCR amplifications were performed on cDNA from tumor cell lines. Total cell line RNAs were reverse transcribed with Superscript II (Life Technologies) and random hexamers. Using the outer primer pair from each amplicon (i.e. 9BP.1A and 9BP.1P or 9BP.2A and 9BP.2P), approximately 10 ng of CDNA from each cell line was amplified for 26 cycles. Products were diluted 60 fold and then reamplified for 22-26 cycles using nested M13 tailed primers (i.e. 9BP.1B and 9BP.21Q or 9BP.2B and 9BP.2Q). Typical primary amplification cycling conditions were an initial denaturation at 95° C. for 60s, followed by 26 cycles of 96° C. (12s), 58° C. (15s) and 72° C. (90s). Typical secondary amplification cycling conditions were an initial denaturation at 95° C. for 60s, followed by 22–26 cycles of 96° C. (12s), 58° C. (15s) and 72° C. (40s). The resulting RT-PCR products were sequenced with dye-primer chemistry on ABI 377 sequencers. Sequences were examined for the presence of variants using the program Sequencher.

The primers used are set forth in Table 3. The sequence variants are set forth in Table 4.

TABLE 3

Table of Primers

| Primer | SEQ ID | Sequence |
|---|---|---|
| 9BP.1A | 13 | GCCACCGCGGGATTAAGTTTCT |
| 9BP.1P | 14 | TGTAGCCAGCAATGGTAATTCCT |
| 9BP.1B | 15 | GTTTTCCCAGTCACGACGGTTCCATTTTAATTGCTGTTAAT |
| 9BP.1Q | 16 | AGGAAACAGCTATGACCATGGGATAATAAAAACGATTCATTT |
| 9BP.1C | 17 | GTTTTCCCAGTCACGACGTTGAATATGCCCACGTTCCTC |
| 9BP.1R | 18 | AGGAAACAGCTATGACCATTCTTTCAATCTTCCATCTCTATG |
| 9BP.1D | 19 | GTTTTCCCAGTCACGACGAACAGAGGAGAGCTGGGAATA |
| 9BP.1S | 20 | AGGAAACAGCTATGACCATCAAACCAGATCCATCATTCACC |
| 9BP.1E | 21 | GTTTTCCCAGTCACGACGGCACAATTTCAGCTCACTCTAA |
| 9BP.1T | 22 | AGGAAACAGCTATGACCATGGATGAGGAGAGGGTGATGC |
| 9BP.2A | 23 | TCTAGCAGGAATGAGCAGTGAG |
| 9BP.2P | 24 | GATCCTGATAATCTAAAATGCTAA |
| 9BP.2B | 25 | GTTTTCCCAGTCACGACGAAGTTGATGATTGCAAGAGGTG |
| 9BP.2Q | 26 | AGGAAACAGCTATGACCATGGTTTGTGCCATCTACTGCTAT |
| 9BP.2C | 27 | GTTTTCCCAGTCACGACGAAAGCAGTGCCGTTGAGCATG |
| 9BP.2R | 28 | AGGAAACAGCTATGACCATGCTGACAGTAATGGATACCCT |
| 9BP.2D | 29 | GTTTTCCCAGTCACGACGGATTTTTTATCTTCGACGAGAAA |
| 9BP.2S | 30 | AGGAAACAGCTATGACCATTTCCCCAAGTAAAGTTATGCCAT |
| 9BP.2E | 31 | GTTTTCCCAGTCACGACGTCCTGTTGGACACAGCGGGA |
| 9BP.2T | 32 | AGGAAACAGCTATGACCATCATGGCCAAAGGTGCTTGAA |
| 9BP.3A | 33 | CCACCCACCACCCAATCAGAAT |
| 9BP.3P | 34 | CATCTCGACTAATGGCACCTCC |
| 9BP.3B | 35 | GTTTTCCCAGTCACGACGGAGACAGAGGATCCAGTGCT |
| 9BP.3Q | 36 | AGGAAACAGCTATGACCATCCCTGACGGTGCTCCCTTCA |
| 9BP.3C | 37 | GTTTTCCCAGTCACGACGTTAACTTGGAAAACAGCAGTCT |
| 9BP.3R | 38 | AGGAAACAGCTATGACCATCATCACCACAAGAACTGCCATG |
| 9BP.3D | 39 | GTTTTCCCAGTCACGACTCTCCTGAAAATGACAGCAT |
| 9BP.3S | 40 | AGGAAACAGCTATGACCATTAAATGAGATTCAGTCCACACT |
| 9BP.3E | 41 | GTTTTCCCAGTCACGACGATAAATGACTACACACCTGCAA |
| 9BP.3T | 42 | AGGAAACAGCTATGACCATAACGATCATCCCCAAGCCATCT |
| 9BP.4A | 43 | CTGAGTACCTGCTTGAACAGAG |
| 9BP.4P | 44 | GACCATTGATCTCTAGAAGCTC |
| 9BP.4B | 45 | GTTTTCCCAGTCACGACGGGACTATTAATATAGCAAAAGGC |
| 9BP.4Q | 46 | AGGAAACAGCTATGACCATCAGTGCCATTACTCTTCCAGA |
| 9BP.4C | 47 | GTTTTCCCAGTCACGACGTACTTATGTGCCTGCAGAACA |
| 9BP.4R | 48 | AGGAAACAGCTATGACCATCATGTTTGATGAAAATGCCCC |
| 9BP.4D | 49 | GTTTTCCCAGTCACGACGATTGTTGGTGGACGAGGGATG |
| 9BP.4S | 50 | AGGAAACAGCTATGACCATCCATTTCGGCAAAGGCTGAAG |
| 9BP.4E | 51 | GTTTTCCCAGTCACGACGCAGAGTCAGAGCCAGAGAAGG |
| 9BP.4T | 52 | AGGAAACAGCTATGACCATAGAAGCTCATCTGCAATTTGC |
| 9BP.5A | 53 | CAGGCGAGCTGCATATGATTG |
| 9BP.5P | 54 | CCTCCTTTGACAATGTCTGACAC |
| 9BP.5B | 55 | GTTTTCCCAGTCACGACGGTGTCTTCATAGTGGGGATTGAT |
| 9BP.5Q | 56 | AGGAAACAGCTATGACCATGAAGCTCCAGATGTTGCACAT |
| 9BP.5C | 57 | GTTTTCCCAGTCACGACGAGAGCCAACTGTTACTACTTC |
| 9BP.5R | 58 | AGGAAACAGCTATGACCATTGAAGGAACAGCCTGGGAATC |
| 9BP.5D | 59 | GTTTTCCCAGTCACGACGTTAGCCTTCTGAAGACAGCAA |
| 9BP.5S | 60 | AGGAAACAGCTATGACCATCATGGATAATAATGGCACCCA |
| 9BP.5E | 61 | GTTTTCCCAGTCACGACGTTTCCAAAGGGGCGAACAGGGC |
| 9BP.5T | 62 | AGGAAACAGCTATGACCATCCAACAATACTTAATCCTAGGC |

TABLE 3-continued

Table of Primers

| Primer | SEQ ID | Sequence |
|---|---|---|
| 9BP.6A | 63 | TGGAATTGACTTGAGAAAGGCCA |
| 9BP.6P | 64 | CCCCCTACAGTTTTGAAGACCC |
| 9BP.6B | 65 | GTTTTCCCAGTCACGACGAAGAGGAGGAAGTGTGTGACAC |
| 9BP.6Q | 66 | AGGAAACAGCTATGACCATGACAGGCTGCCTTCACTCACC |
| 9BP.6C | 67 | GTTTTCCCAGTCACGACGTCAAAGCTGGTCCATTCCATT |
| 9BP.6R | 68 | AGGAAACAGCTATGACCATGGATGTGCCACAGATGGTGAC |
| 9BP.6D | 69 | GTTTTCCCAGTCACGACGATGATGCACCCAACTGGAGTT |
| 9BP.6S | 70 | AGGAAACAGCTATGACCATGGCTGCCATATCCTCCAACTA |
| 9BP.6E | 71 | GTTTTCCCAGTCACGACGGGACCTCCTCAATGTAAGTCT |
| 9BP.6T | 72 | AGGAAACAGCTATGACCATATTGTCAGGACCAGTGCATTC |

TABLE 4

Sequence Variants

| Cell line | Type | nt variant | aa change | note |
|---|---|---|---|---|
| LNCAP.FGC | prostatic | G163A | val->ile | heterozygous |
| OV-1063 | ovarian | G343T | gly->trp | non-het* |
| UACC812 | breast | A1074G | thr->thr | heterozygous |
| UACC8933 | breast | G5624A | arg->lys | non-het* |
| HS776T | pancreatic | G5624A | arg->lys | non-het* |

*In mutation screening from cDNA, a non-heterozygous call for a sequence variant is consistent with non-expression of one allele, hemizygosity at that position, or homozygosity at that position.

Example 6

Generation of Polyclonal Antibody Against MMSC2

Segments of MMSC2 coding sequence are expressed as fusion protein in *E. coli*. The overexpressed protein is purified by gel elution and used to immunize rabbits and mice using a procedure similar to the one described by Harlow and Lane, 1988. This procedure has been shown to generate Abs against various other proteins (for example, see Kraemer et al., 1993).

Briefly, a stretch of MMSC2 coding sequence is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. Identification of the protein as the MMSC2 fusion product is verified by protein sequencing at the N-terminus. Next, the purified protein is used as immunogen in rabbits. Rabbits are immunized with 100 μg of the protein in complete Freund's adjuvant and boosted twice in 3 week intervals, first with 100 μg of immunogen in incomplete Freund's adjuvant followed by 100 μg of immunogen in PBS. Antibody containing serum is collected two weeks thereafter. This procedure is repeated to generate antibodies against the mutant forms of the MMSC2 gene product. These antibodies, in conjunction with antibodies to wild type MMSC2, are used to detect the presence and the relative level of the mutant forms in various tissues and biological fluids.

Example 7

Generation of Polyclonal Antibody Against MMSC2-MMSC2 Interacting Protein Complex MMSC2 is capable of binding to certain proteins, e.g., MMAC1. A complex of the two proteins is prepared, e.g., by mixing purified preparations of each of the two proteins. If desired, the protein complex can be stabilized by cross-linking the proteins in the complex by methods known to those of skill in the art. The protein complex is used to immunize rabbits and mice using a procedure similar to the one described by Harlow and Lane, 1988. This procedure has been shown to generate Abs against various other proteins (for example, see Kraemer et al., 1993).

Briefly, the purified protein complex is used as immunogen in rabbits. Rabbits are immunized with 100 pg of the protein in complete Freund's adjuvant and boosted twice in 3 week intervals, first with 100 μg of immunogen in incomplete Freund's adjuvant followed by 100 μg of immunogen in PBS. Antibody containing serum is collected two weeks thereafter.

This procedure is repeated to generate antibodies against forms of the complex which comprise mutant MMSC2 or mutant MMSC2 interacting protein (e.g)., mutant MMAC1). These antibodies, in conjunction with antibodies to wild type MMSC2 or MMSC2 interacting protein (e.g., MMAC1), are used to detect the presence and the relative level of the mutant forms in various tissues and biological fluids.

Example 8

Generation of Monoclonal Antibodies Specific for MMSC2

Monoclonal antibodies are generated according to the following protocol. Mice are immunized with immunogen comprising intact MMSC2 or MMSC2 peptides (wild type or mutant) conjugated to keyhole limpet hemocyanin using glutaraldehyde or EDC as is well known.

The immunogen is mixed with an adjuvant. Each mouse receives four injections of 10 to 100 μg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lanc, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of MMSC2 specific antibodies by ELISA or RIA using wild type or mutant MMSC2 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

Example 9

Generation of Monoclonal Antibodies Specific for MMSC2-MMSC2 Interacting Protein Complex Monoclonal antibodies are generated according to the following protocol. Mice are immunized with immunogen comprising MMSC2-MMSC2 interacting protein complexes (wild type or mutant), such as MMAC1, conjugated to keyhole limpet hemocyanin using glutaraldehyde or EDC as is well known. The complexes may be stabilized by cross-linking.

The immunogen is mixed with an adjuvant. Each mouse receives four injections of 10 to 100 µg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of MMSC2-MMSC2 interacting protein complex specific antibodies by ELISA or RIA using wild type or mutant MMSC2-MMSC2 interacting protein complexes as target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development. Antibodies are tested for binding to MMSC2 alone or to MMSC2 interacting protein alone to determine which are specific for the complex as opposed to binding to the individual proteins.

Example 10

Sandwich Assay for MMSC2

Monoclonal antibody is attached to a solid surface such as a plate, tube, bead or particle. Preferably, the antibody is attached to the well surface of a 96-well ELISA plate. 100 µL sample (e.g., serum, urine, tissue cytosol) containing the MMSC2 peptide/protein (wild-type or mutants) is added to the solid phase antibody. The sample is incubated for 2 hrs at room temperature. Next the sample fluid is decanted, and the solid phase is washed with buffer to remove unbound material. 100 µL of a second monoclonal antibody (to a different determinant on the MMSC2 peptide/protein) is added to the solid phase. This antibody is labeled with a detector molecule (e.g., $^{125}$I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of MMSC2 peptide/protein present in the sample, is quantified. Separate assays are performed using monoclonal antibodies which are specific for the wild-type MMSC2 as well as monoclonal antibodies specific for each of the mutations identified in MMSC2.

Example 11

Sandwich Assay for MMAC1 Using MMSC2

MMSC2 or PDZ domain 7 of MMSC2 is attached to a solid surface such as a plate, tube, bead or particle. Preferably, MMSC2 or its PDZ domain is attached to the well surface of a 96-well ELISA plate. 100 µL sample (e.g., serum, urine, tissue cytosol) containing the MMAC1 peptide/protein (wild-type or mutants) is added to the solid phase MMSC2. The sample is incubated for 2 hrs at room temperature. Next the sample fluid is decanted, and the solid phase is washed with buffer to remove unbound material. 100 µL of a monoclonal antibody to MMAC1 is added to the solid phase. The antibody is labeled with a detector molecule (e.g., $^{125}$I, enzyme, fluorophore, or a chromophore) and the solid phase with the antibody is incubated for two hrs at room temperature. The antibody is decanted and the solid phase is washed with buffer to remove unbound material. The amount of bound label, which is proportional to the amount of wild-type MMAC1 present in the sample, is quantified.

Example 12

Drug Screening

The invention is useful in screening for drugs which can overcome mutations in MMSC2 and also mutations in MMAC1. The knowledge that MMSC2 and MMAC1 form a complex is useful in designing such assays. If a mutation is present in either MMSC2 or in MMAC1 which prevents the MMSC2-MMAC1 complex from forming, drugs may be screened which will overcome the mutation and allow the protein complex to form and to be active. Such screening assays can be, e.g., a yeast two hybrid assay which is dependent upon two proteins interacting. In such an assay, the presence of a mutant protein may show no activity or low activity in such an assay, while the presence of a useful drug will result in formation of a proper complex which results in activity in the assay.

A simple binding assay which shows the binding, i.e., formation of a complex, can similarly be used as outlined above. Useful drugs will increase the formation of MMSC2-MMAC1 complexes. Antibodies may also be used to monitor the amount of complex present. Antibodies specific for the complex are especially useful. If the presence of a drug increases the amount of complex present then the drug is a good candidate for treating the cancer which is a result of the mutation in either the MMSC2 or the MMAC1.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Anand, R. (1992). *Techniques for the Analysis of Complex Genomes,* (Academic Press).
Anderson, et al. (1980). *Proc. Natl. Acad. Sci. USA* 77:5399–5403.
Ausubel, F. M., et al. (1992). *Current Protocols in Molecular Biology,* (J. Wiley and Sons, N.Y.)
Bartel, P. L. and Fields, S. (1995). *Methods in Enzymology* 254:241–263.
Bartel, P. L. et al. (1993). "Using the 2-hybrid system to detect protein-protein interactions." In *Cellular Interactions in Development: A Practical Approach,* Oxford University Press, pp. 153–179.
Beaucage and Carruthers (1981). *Tetra. Letts.* 22:1859–1862.
Berglund, P. et al. (1993) *Biotechnology* 11:916–920
Berkner, et al. (1988). *BioTechniques* 6:616–629.
Berkner (1992). *Curr. Top. Microbiol. Immunol.* 158:39–61.
Borman, S. (1996). *Chemical & Engineering News,* December 9 issue, pp. 42–43.
Brandyopadhyay and Temin (1984). *Mol. Cell Biol.* 4:749–754.
Breakfield and Geller (1987). *Mol. Neurobiol.* 1:337–371.
Breeden, L., and Naysmyth, K. (1985). *Cold Spring Harbor Symp. Quant. Biol.* 50:643–650.
Brenman, J. E. et al. (1996). *Cell* 84:757–767.
Brinster, et al. (1981). *Cell* 27,:223–231.
Buchschacher and Panganiban (1992). *J. Virol.* 66:2731–2739.
Capecchi, M. R. (1989). *Science* 244:1288.
Cariello (1988). *Human Genetics* 42:726.
Chee, M., et al. (1996). *Science* 274:610–614.
Chevray, P. M. & Nathans, D. N. (1992). *Proc. Natl. Acad. Sci. USA* 89:5789–5793.
Cho, K. O. et al. (1992). *Neuron* 9:929–942.
Compton, J. (1991). "Nucleic acid sequence-based amplification." *Nature* 350:91–92.
Conner, B. J., et al. (1983). *Proc. Natl. Acad. Sci. USA* 80:278–282.
Constantini and Lacy (1981). *Nature* 294:92–94.
Cotten, M., et al. (1990). *Proc. Natl. Acad. Sci. USA* 87:4033–4037.
Cotton, R. G., et al. (1988). *Proc. Natl. Acad Sci. USA* 85:4397–4401.
Culver, K. (1996). *Gene Therapy: A Primer for Physicians,* 2nd Ed., Mary Ann Liebert.
Curiel, et al. (1991a). *Hum. Gene Ther.* 3:147–154.
Curiel, et al. (1991 b). *Proc. Natl. Acad. Sci. USA* 88:8850–8854.
Deutscher, M. (1990). *Meth. Enzymology* 182 (Academic Press, San Diego, Calif.).
Donehower, L. A., et al. (1992). *Nature* 356:215.
Editorial (1996). *Nature Genetics* 14:367–370.
Elghanian, R., et al. (1997). *Science* 277:1078–1081.
*Enhancers and Eukaryotic Gene Expression,* Cold Spring Harbor Press, Cold Spring Harbor, N.Y. (1983).
Erickson, J., et al. (1990). *Science* 249:527–533.
Fahy, E., et al. (1991). *PCR Methods Appl.* 1:25–33.
Feigner, et al. (1987). *Proc. Natl. Acad. Sci. USA* 84:7413–7417.
Fields, S. & Song, O.-K. (1989). *Nature* 340:245–246.
Fiers, et al. (1978). *Nature* 273:113.
Fink, et al. (1992). *Hum. Gene Ther.* 3:11–19.
Fink, D. J. et al. (1996). *Ann. Rev. Neurosci.* 19:265–287.
Finkelstein, J., et al. (1990). *Genomics* 7:167–172.
Fodor, S. P. A. (1997). DNA Sequencing. Massively Parallel Genomics. *Science* 277:393–395.
Freese, et al. (1990). *Biochem. Pharmacol.* 40:2189–2199.
Friedman, T. (1991). In *Therapy for Genetic Diseases,* T. Friedman, ed., Oxford University Press, pp. 105–121.
Furnari, F. B. et al. (1997). *Proc. Natl. Acad. Sci. USA* 94:12479–12484.
Gietz, R. D., et al. (1995). *Yeast* 11:355–360.
Glover, D. (1985). *DNA Cloning,* I and II (Oxford Press).
Goding (1986). *Monoclonal Antibodies: Principles and Practice,* 2d ed. (Academic Press, N.Y.).
Godowski, et al. (1988). *Science* 241:812–816.
Gordon, et al. (1980). *Proc. Natl. Acad. Sci. USA* 77:7380–7384.
Gorziglia and Kapikian (1992). *J. Virol.* 66:4407–4412.
Graham and van der Eb (1973). *Virology* 52:456–467.
Grompe, M. (1993). *Nature Genetics* 5:111–117.
Grompe, M., et al. (1989). *Proc. Natl. Acad. Sci. USA* 86:5855–5892.
Guthrie, G. and Fink, G. R. (1991). *Guide to Yeast Genetics and Molecular Biology* (Academic Press).
Hacia, J. G., et al. (1996). *Nature Genetics* 14:441–447.
Harlow and Lane (1988). *Antibodies: A Laboratory Manual* (Cold Spring Harbor Laboratory, Cold Spring Harbor, N.Y.).
Harrison, S. C. (1996). *Cell* 86:341–343.
Hasty, P., K., et al. (1991). *Nature* 350:243.
Helseth, et al. (1990). *J. Virol.* 64:2416–2420.
Hodgson, J. (1991). *Bio/Technology* 9:19–21.
Huse, et al. (1989). *Science* 246:1275–1281.
Innis, et al. (1990). *PCR Protocols: A Guide to Methods and Applications* (Academic Press, San Diego, Calif.).
Jablonski, E., et al. (1986). *Nucl. Acids Res.* 14:6115–6128.
Jakoby, W. B. and Pastan, I. H. (eds.) (1979). Cell Culture. *Methods in Enzymology,* volume 58 (Academic Press, Inc., Harcourt Brace Jovanovich (New York)).
Johnson, et al. (1992). *J. Virol* 66:2952–2965.
Johnson, et al. (1993). "Peptide Turn Mimetics" in *Biotechnology and Pharmacy,* Pezzuto et al., eds., Chapman and Hall, New York.
Kaneda, et al. (1989). *J. Biol. Chem.* 264:12126–12129.
Kanehisa (1984). *Nucl. Acids Res.* 12:203–213.
Kavanaugh, W. M. et al. (1995). *Science* 268:1177–1179.
Kennedy, M. B. (1995). *Trends Biochem. Sci.* 20:350.
Kinszler, K. W., et al. (1991). *Science* 251:1366–1370.
Kohler, G. and Milstein, C. (1975). *Nature* 256:495–497.
Kong, D. et al. (1997). *Nature Genetics* 17:143–144.
Kornau, H. C. et al. (1995). *Science* 269:1737–1740.
Kraemer, F. B. et al. (1993). *J. Lipid Res.* 34:663–672.
Kubo, T., et al. (1988). *FEBS Letts.* 241:119.
Kyte, J. & Dolittle, R. F. (1982). *J. Mol. Bio.* 157:105–132.
Landegren, et al. (1988). *Science* 242:229.
Lee, J. E. et al. (1995). *Science* 268:836–844.
Lemmon, M. A. et al. (1996). *Cell* 85:621–624.
Li, D. M. & Sun, H. (1997). *Cancer Res.* 57:2124–2129.
Li, J. et al. (1997). *Science* 275:1943–1947.
Liaw, D. et al. (1997). *Nature Genetics* 16:64–67.
Lim, et al. (1992). *Circulation* 83:2007–2011.
Lipshutz, R. J., et al. (1995). *Biotechniques* 19:442–447.
Lockhart, D. J., et al. (1996). *Nature Biotechnology* 14:1675–1680.
Louis, D. N. & Gusella, J. F. (1995). *Trends. Genet.* 11:412–415.
Madzak, et al. (1 992). *J. Gen. Virol.* 73:1533–1536.
Maldonado, E., et al. (1996). *Nature* 381:86–89.
Maniatis, T. et al. (1982). *Molecular Cloning: A Laboratory Manual* (Cold Spring Harbor Laboratory, Cold Spring Harbor, N.Y.).
Mann and Baltimore (1985). *J. Virol.* 54:401–407.

Margolskee (1992). *Curr. Top. Aicrobiol. Immunol.* 158:67–90.
Marsh, D. J. et al. (1997). *Nature Genetics* 16:333–334.
Martin, R., et al. (1990). *BioTechniques* 9:762–768.
Matteucci, M. D. and Caruthers, M. H. (1981). *J. Am. Chem. Soc.* 103:3185.
Matthews and Kricka (1988). *Anal. Biochem.* 169:1.
Merrifield (1963). *J. Am. Chem. Soc.* 85:2149–2156.
Metzger, et al. (1988). *Nature* 334:31–36.
Miller (1992). *Curr. Top. Microbiol. Immunol.* 158:1–24.
Miller, et al. (1985). *Mol. Cell. Biol.* 5:431–437.
Miller, et al. (1988). *J. Virol.* 62:4337–4345.
Modrich, P. (1991). *Ann. Rev. Genet.* 25:229–253.
Mombaerts, P., et al. (1992). *Cell* 68:869.
Moss (1992). *Curr. Top. Microbiol. Immunol.* 158:25–38.
Moss, B. (1996). *Proc. Natl. Acad. Sci. USA* 93:11341–11348.
Muzyczka (1992). *Curr. Top. Microbiol. Immunol.* 158:97–123.
Nabel, et al. (1990). *Science* 249:1285–1288.
Nabel (1992). *Hum. Gene Ther.* 3:399–410.
Naldini, L. et al. (1996). *Science* 272:263–267.
Nelen, M. R. et al. (1997). *Hum. Mol. Genet.* 6:1383–1387.
Newton, C. R., et al. (1989). *Nucl. Acids Res.* 17:2503–2516.
Nguyen, Q., et al. (1992). *BioTechniques* 13:116–123.
Novack, et al. (1986). *Proc. Natl. Acad. Sci. USA* 83:586.
Ohi, et al. (1990). *Gene* 89:279–282.
Olschwang, S. et al. (1998). *Nature Genetics* 18:12–13.
Orita, M., et al. (1989). *Proc. Natl. Acad. Sci. USA* 86:2766–2770.
Page, et al. (1990). *J. Virol.* 64:5370–5276.
Pawson, T. (1994). *Adv. Cancer Res.* 64:87–110.
Pawson, T. & Scott, J. D. (1997). *Science* 278:2075–2080.
Pellicer, et al. (1980). *Science* 209:1414–1422.
Petropoulos, et al. (1992). *J. Virol.* 66:3391–3397.
Philpott, K. L., et al. (1992). *Science* 256:1448.
Quantin, et al. (1992). *Proc. Natl. Acad. Sci. USA* 89:2581–2584.
Rano and Kidd (1989). *Nucl Acids Res.* 17:8392.
*Remington's Pharmaceutical Sciences,* 18th Ed. (1990, Mack Publishing Co., Easton, Pa.).
Rigby, P. W. J., et al. (1977). *J. Mol. Biol.* 113:237–251.
Rosenfeld, et al. (1992). *Cell* 68:143–155.
Russell, D. & Hirata, R. (1998). *Nature Genetics* 18:323–328.
Sambrook, J., et al. (1989). *Molecular Cloning: A Laboratory Manual,* 2nd Ed. (Cold Spring Harbor Laboratory, Cold Spring Harbor, N.Y.).
Sande, S., and Privalsky, M. L. (1996). *Molecular Endocrin.* 10:813–825.
Scharf (1986). *Science* 233:1076.
Schiessinger, J. (1994). "SH2/SH3 signaling proteins." *Curr. Opin. Genet. Dev.* 4:25–30.
Schneider, G. et al. (1998). *Nature Genetics* 18:180–183.
Scopes, R. (1982). *Protein Purification: Principles and Practice,* (Springer-Verlag, N.Y.).
Shaw, G. (1996). *Bioessays* 18:35–46.
Sheffield, V. C., et al. (1989). *Proc. Natl. Acad. Sci. USA* 86:232–236.
Sheffield, V. C., et al., (1991). *Am. J. Hum. Genet.* 49:699–706.
Shenk, T. E., et al. (1975). *Proc. Natl. Acad. Sci. USA* 72:989–993.
Shieh, B. & Zhu, M. (1996). *Neuron* 16:991–998.
Shimada, et al. (1991). *J. Clin. Invest.* 88:1043–1047.
Shinkai, Y., et al. (1992). *Cell* 68:855.
Shoemaker, D. D., et al. (1996). *Nature Genetics* 14:450–456.
Snouwaert, J. N., et al. (1992). *Science* 257:1083.
Songyang, Z. et al. (1997). *Science* 275:73–77.
Sorge, et al. (1984). *Mol. Cell. Biol.* 4:1730–1737.
Spargo, C. A., et al. (1996). *Mol. Cell. Probes* 10:247–256.
Steck, P. A. et al. (1997). *Nature Genetics* 15:356–362.
Stewart, et al. (1992). *Hum. Gene Ther.* 3:267–275.
Stratford-Perricaudet, et al. (1990). *Hum. Gene Ther.* 1:241–256.
Tsunoda, S. et al. (1997). *Nature* 388:243–249.
Valancius, V. and Smithies, O. (1991). *Mol. Cell. Biol.* 11:1402.
van der Greer, P. & Pawson, T. (1995). *Trends Biochem. Sci.* 20:277–280.
Wagner, et al. (1991). *Proc. Natl. Acad. Sci. USA* 88:4255–4259.
Wagner, et al. (1990). *Proc. Natl. Acad. Sci. USA* 87:3410–3414.
Walker, G. T., et al. (1992). *Nucl. Acids Res.* 20:1691–1696.
Wang and Huang (1989). *Biochemistry* 28:9508–9514.
Wartell, R. M., et al. (1990). *Nucl. Acids Res.* 18:2699–2705.
Wells, J. A. (1991). *Methods in Enzymol.* 202:390–411.
Wetmur and Davidson (1968). *J. Mol. Biol.* 31:349–370.
White, M. B., et al. (1992). *Genomics* 12:301–306.
White and Lalouel (1988). *Ann. Rev. Genet.* 22:259–279.
Wilkinson, et al. (1992). *Nucleic Acids Res.* 20:2233–2239.
Wolff, et al. (1990). *Science* 247:1465–1468.
Wolff, et al. (1991). *BioTechniques* 11:474–485.
Woods, D. F. & Bryant, P. J. (1991). *Cell* 66:451–464.
Woods, D. F. & Bryant, P. J. (1993). *Mech. Dev.* 44:5–89.
Wu, et al. (1989a). *Genomics* 4:560–569.
Wu, et al. (1989 b). *J. Biol. Chem.* 264:16985–16987.
Wu, et al. (1991). *J. Biol. Chem.* 266:14338–14342.
Zenke, et al. (1990). *Proc. Natl. Acad. Sci. USA* 87:3655–3659.

PATENTS AND PATENT APPLICATIONS

Geysen, H., published PCT application WO 84/03564, published Sep. 13, 1984 Hitzeman et al., EP 73,675A.
EP 225,807A.
EP 332,435A.
EP425,731 A
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,376,110.
U.S. Pat. No. 4,486,530.
U.S. Pat. No. 4,554,101
U.S. Pat. No. 4,683,195
U.S. Pat. No. 4,683,202
U.S. Pat. No. 4,816,567
U.S. Pat. No. 4,868,105.
U.S. Pat. No. 5,252,479.
U.S. Pat. No. 5,270,184.
U.S. Pat. No. 5,409,818.
U.S. Pat. No. 5,455,166.
U.S. Pat. No. 5,550,050
U.S. Pat. No. 5,691,198
WO 90/07936
WO 92/19195
WO 93/07282.
WO 94/25503
WO 95/01203
WO 95/05452

WO 96/02286
WO 96/02646
WO 96/40871

WO 96/40959
WO 97/02048
WO 97/12635

What is claimed is:

1. An isolated nucleic acid encoding an MMSC2 polypeptide, wherein said MMSC2 polypeptide comprises the contiguous amino acid sequence set forth in SEQ ID NO: 3.

2. The isolated nucleic acid of claim 1, wherein said nucleic acid comprises the nucleotide sequence set forth in SEQ ID NO: 2 or the complement of SEQ ID NO: 2 and wherein said nucleic acid is DNA or a corresponding RNA.

3. An expression vector comprising the isolated nucleic acid of claim 1 wherein said nucleic acid is operably linked to suitable control sequences which can direct the expression of said nucleic acid in host cells for said expression vector.

4. A host cell transformed with the vector of claim 3.

5. A method of producing an MMSC2 polypeptide having the amino acid sequence set forth in SEQ ID NO:3, wherein said method comprises: (i) culturing the host cell of claim 4 under conditions suitable for the production of said MMSC2 polypeptide and (ii) recovering said MMSC2 polypeptide.

6. An isolated nucleic acid encoding a mutated MMSC2 polypeptide, wherein said nucleic acid comprises an allelic variant of the nucleotide sequence set forth in SEQ ID NO:2, wherein said allelic variant is selected from the group consisting of: an A at base 219; a T at base 399; a G at base 1130; and an A at base 5680.

7. The nucleic acid of claim 6, wherein said nucleic acid is DNA.

8. The nucleic acid of claim 6, wherein said nucleic acid is RNA.

9. An isolated nucleic acid complementary to said nucleic acid of claim 7.

10. A pair of single-stranded oligonucleotide primers for determination of a nucleotide sequence of a MMSC2 gene by a nucleic acid amplification reaction, wherein using said primers in a nucleic acid amplification reaction results in the synthesis of DNA or RNA corresponding to all or part of the sequence of the MMSC2 gene, wherein said pair is selected from the group consisting of: SEQ ID NO:13 and SEQ ID NO:14; SEQ ID NO:15 and SEQ ID NO:16; SEQ ID NO:17 and SEQ ID NO:18; SEQ ID NO:19 and SEQ ID NO:20; SEQ ID NO:21 and SEQ ID NO:22; SEQ ID NO:23 and SEQ ID NO:24; SEQ ID NO:25 and SEQ ID NO:26; SEQ ID NO:27 and SEQ ID NO:28; SEQ ID NO:29 and SEQ ID NO:30; SEQ ID NO:31 and SEQ ID NO:32; SEQ ID NO:33 and SEQ ID NO:34; SEQ ID NO:35 and SEQ ID NO:36; SEQ ID NO:37 and SEQ ID NO:38; SEQ ID NO:39 and SEQ ID NO:40; SEQ ID NO:41 and SEQ ID NO:42; SEQ ID NO:43 and SEQ ID NO:44; SEQ ID NO:45 and SEQ ID NO:46; SEQ ID NO:47 and SEQ ID NO:48; SEQ ID NO:49 and SEQ ID NO:50; SEQ ID NO:51 and SEQ ID NO:52; SEQ ID NO:53 and SEQ ID NO:54; SEQ ID NO:55 and SEQ ID NO:56; SEQ ID NO:57 and SEQ ID NO:58; SEQ ID NO:59 and SEQ ID NO:60; SEQ ID NO:61 and SEQ ID NO:62; SEQ ID NO:63 and SEQ ID NO:64; SEQ ID NO:65 and SEQ ID NO:66; SEQ ID NO:67 and SEQ ID NO:68; SEQ ID NO:69 and SEQ ID NO:70; and SEQ ID NO:71 and SEQ ID NO:72.

11. A method for identifying a mutation in a suspected mutant MMSC2 allele, wherein said method comprises comparing a nucleotide sequence of the suspected mutant MMSC2 allele with a nucleotide sequence of a wild-type MMSC2 of SEQ ID NO:2, and wherein a difference between the nucleotide sequence of the suspected mutant MMSC2 allele and the nucleotide sequence of the wild-type MMSC2 identifies said mutation in said suspected mutant MMSC2 allele.

12. A method for detecting an alteration in a MMSC2 gene of a subject as compared to SEQ ID NO:2 wherein said alteration is associated with a cancer in said subject, wherein said method comprises analyzing a nucleotide sequence of said MMSC2 gene or mRNA of said MMSC2 gene from a tissue sample of said subject.

13. A method according to claim 12, wherein the nucleotide sequence of said MMSC2 gene is compared with the nucleotide sequence of MMSC2 gene set forth in SEQ ID NO:2.

14. The method of claim 12, wherein said method comprises analyzing said mRNA.

15. The method of claim 12, wherein said analyzing comprises one or more of the following procedures:

(a) observing a difference in electrophoretic mobility of a single-stranded DNA probe of said MMSC2 gene from said tissue sample as compared to electrophoretic mobility of a wild-type single-stranded DNA probe of MMSC2 gene disclosed in SEQ ID NO:2 as measured by distance said single-stranded DNA probe of said MMSC2 gene from said tissue sample and distance said wild-type single-stranded DNA probe have moved on non-denaturing polyacrylamide gels;

(b) hybridizing a MMSC2 gene probe comprising SEQ ID NO:2 or a fragment thereof to genomic DNA isolated from said tissue sample under stringent hybridization conditions comprising performing the hybridization at 45° C. in the presence of 200 mM salt;

(c) determining hybridization of an allele-specific probe comprising SEQ ID NO:2 or a fragment thereof to genomic DNA from said tissue sample wherein said allele-specific probe is labeled with a detectable signal and said detectable signal is detected;

(d) amplifying all or part of the MMSC2 gene from said sample to produce an amplified sequence, sequencing the amplified sequence and comparing the nucleotide sequence of said amplified sequence with the sequence of SEQ ID NO:2;

(e) determining by nucleic acid amplification the presence of a specific mutant allele of MMSC2 in said tissue sample wherein, in comparison to the nucleotide sequence of SEQ ID NO:2, said mutant allele has a change in its nucleotide sequence, wherein said change is selected from the group consisting of: an A at base 219, a T at base 399, a G at base 1130 and an A at base 5680, wherein said amplification is performed using a primer which will hybridize only to said specific MMSC2 mutant allele thereby allowing amplification only if said mutant allele is present;

(f) molecularly cloning all or part of the MMSC2 gene from said tissue sample by isolating said all or part of the MMSC2 gene and ligating it within a vector to produce a cloned sequence and sequencing the cloned sequence;

(g) determining whether there is a mismatch between molecules (1) MMSC2 gene genomic DNA or MMSC2 mRNA isolated from said tissue sample, and (2) a nucleic acid riboprobe complementary to the human wild-type MMSC2 gene DNA of SEQ ID NO:2, when molecules (1) and (2) are hybridized to each other to form a duplex, said method comprising treating said duplex with an RNAse which nicks said duplex at mismatched bases and determining whether a nick has occurred by determining sizes of said molecules following denaturation of said duplex;

(h) amplifying a MMSC2 gene sequence in said tissue sample and hybridizing the amplified sequence to a nucleic acid probe wherein said nucleic acid probe comprises a nucleotide sequence of SEQ ID NO:2 or a fragment thereof;

(i) amplifying a MMSC2 gene sequence in said tissue sample and hybridyzing the amplified sequence to a nucleic acid probe wherein said nucleic acid probe comprises a nucleotide sequence of a mutant MMSC2 gene, wherein, in comparison to the nucleotide sequence of SEQ ID NO:2, said mutant MMSC2 gene sequence comprises a mutation in its nucleotide sequence, wherein said mutation is selected from the group consisting of: an A at base 219; a T at base 399; a G at base 1130; and an A at base 5680;

(j) screening for a deletion mutation by analyzing an MMSC2 gene or an MMSC2 mRNA from said tissue sample of said subject;

(k) screening for a point mutation by analyzing an MMSC2 gene or an MMSC2 mRNA from said tissue sample of said subject;

(l) screening for an insertion mutation by analyzing an MMSC2 gene or an MMSC2 mRNA from said tissue sample of said subject; and (m) determining in situ hybridization of the MMSC2 gene in said tissue sample with one or more nucleic acid probes which comprise the MMSC2 gene sequence of SEQ ID NO:2 or a mutant MMSC2 gene sequence, wherein said mutant MMSC2 gene sequence, based on SEQ ID NO:2, comprises a mutation selected from the group consisting of: an A at base 219; a T at base 399; a G at base 1130; and an A at base 5680, wherein said nucleic acid probes are hybridized to said tissue sample.

16. A replicative cloning vector comprising the isolated nucleic acid of claim 1 and a replicon operative in a host cell.

17. A pair of primers as claimed in claim 10 for determination of all or part of the sequence of the MMSC2 gene having the nucleotide sequence set forth in SEQ ID NO:2, allelic variant or a mutated form thereof.

\* \* \* \* \*

SEQUENCE LISTING

<160> NUMBER OF SEQ ID NOS: 72

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:Consensus
      motif for interaction of PDZ domains.
<220> FEATURE:
<221> NAME/KEY: PEPTIDE
<222> LOCATION: (2)..(4)
<223> OTHER INFORMATION: Xaa at residue 2 may be Ser or Thr; Xaa at
      residue 3 may be any amino acid; Xaa at residue 4 may be
      Val or Ile.

<400> SEQUENCE: 1

Glu Xaa Xaa Xaa
  1

<210> SEQ ID NO 2
<211> LENGTH: 7431
<212> TYPE: DNA
<213> ORGANISM: Homo sapiens
<220> FEATURE:
<221> NAME/KEY: CDS
<222> LOCATION: (57)..(6167)

<400> SEQUENCE: 2

```
gttccatttt aattgctgtt aatcatttca gagaagaaca ctgaactttg aaaaaa atg     59
                                                                 Met
                                                                   1 ttg gaa gcc att gac aaa aat cgg gcc ctg cat gca gca gag cgc ttg      107
Leu Glu Ala Ile Asp Lys Asn Arg Ala Leu His Ala Ala Glu Arg Leu
            5                  10                  15 caa acc aag ctg cga gaa cgt ggg gat gta gca aat gaa gac aaa ctg      155
Gln Thr Lys Leu Arg Glu Arg Gly Asp Val Ala Asn Glu Asp Lys Leu
        20                  25                  30 agc ctt ctg aag tca gtc ctg cag agc cct ctc ttc agt cag att ctg      203
Ser Leu Leu Lys Ser Val Leu Gln Ser Pro Leu Phe Ser Gln Ile Leu
    35                  40                  45 agc ctt cag act tct gta cag cag ctg aaa gac cag gta aat att gca      251
Ser Leu Gln Thr Ser Val Gln Gln Leu Lys Asp Gln Val Asn Ile Ala
50                  55                  60                  65 act tca gca act tca aat att gaa tat gcc cac gtt cct cat ctc agc      299
Thr Ser Ala Thr Ser Asn Ile Glu Tyr Ala His Val Pro His Leu Ser
                70                  75                  80 cca gct gtg att cct act ctg caa aat gaa tcg ttt tta tta tcc cca      347
Pro Ala Val Ile Pro Thr Leu Gln Asn Glu Ser Phe Leu Leu Ser Pro
            85                  90                  95 aac aat ggg aat ctg gaa gca ctt aca gga cct ggt att cca cac att      395
Asn Asn Gly Asn Leu Glu Ala Leu Thr Gly Pro Gly Ile Pro His Ile
        100                 105                 110 aat ggg aaa cct gct tgt gat gaa ttt gat cag ctt atc aaa aat atg      443
Asn Gly Lys Pro Ala Cys Asp Glu Phe Asp Gln Leu Ile Lys Asn Met
    115                 120                 125 gcc cag ggt cgc cat gta gaa gtt ttt gag ctc ctc aaa cct cca tct      491
Ala Gln Gly Arg His Val Glu Val Phe Glu Leu Leu Lys Pro Pro Ser
130                 135                 140                 145
```

```
gga ggc ctt ggg ttt agt gtt gtg gga cta aga agt gaa aac aga gga       539
Gly Gly Leu Gly Phe Ser Val Val Gly Leu Arg Ser Glu Asn Arg Gly
                150                 155                 160 gag ctg gga ata ttt gtt caa gag ata caa gag ggc agt gtg gcc cat       587
Glu Leu Gly Ile Phe Val Gln Glu Ile Gln Glu Gly Ser Val Ala His
        165                 170                 175 aga gat gga aga ttg aaa gaa act gat caa att ctt gct atc aat gga       635
Arg Asp Gly Arg Leu Lys Glu Thr Asp Gln Ile Leu Ala Ile Asn Gly
            180                 185                 190 cag gct ctt gat cag aca att aca cat cag cag gct atc agc atc ctg       683
Gln Ala Leu Asp Gln Thr Ile Thr His Gln Gln Ala Ile Ser Ile Leu
    195                 200                 205 cag aaa gcc aaa gat act gtc cag cta gtt att gcc aga ggc tca ttg       731
Gln Lys Ala Lys Asp Thr Val Gln Leu Val Ile Ala Arg Gly Ser Leu
210                 215                 220                 225 cct cag ctt gtc agc ccc ata gtt tcc cgt tct cca tct gca gcc agc       779
Pro Gln Leu Val Ser Pro Ile Val Ser Arg Ser Pro Ser Ala Ala Ser
                230                 235                 240 aca att tca gct cac tct aat ccg gtt cac tgg caa cac atg gaa acg       827
Thr Ile Ser Ala His Ser Asn Pro Val His Trp Gln His Met Glu Thr
            245                 250                 255 att gaa ttg gtg aat gat gga tct ggt ttg gga ttt ggc atc ata gga       875
Ile Glu Leu Val Asn Asp Gly Ser Gly Leu Gly Phe Gly Ile Ile Gly
        260                 265                 270 gga aaa gca act ggt gtg ata gta aaa acc att ctg cct gga gga gta       923
Gly Lys Ala Thr Gly Val Ile Val Lys Thr Ile Leu Pro Gly Gly Val
    275                 280                 285 gct gat cag cat ggg cgt tta tgc agt gga gac cac att cta aag att       971
Ala Asp Gln His Gly Arg Leu Cys Ser Gly Asp His Ile Leu Lys Ile
290                 295                 300                 305 ggt gac aca gat cta gca gga atg agc agt gag caa gta gca caa gtc      1019
Gly Asp Thr Asp Leu Ala Gly Met Ser Ser Glu Gln Val Ala Gln Val
                310                 315                 320 ctt agg caa tgt gga aat aga gtt aag ttg atg att gca aga ggt gcc      1067
Leu Arg Gln Cys Gly Asn Arg Val Lys Leu Met Ile Ala Arg Gly Ala
            325                 330                 335 ata gaa gaa cgt aca gca ccc act gct ttg ggc atc acc ctc tcc tca      1115
Ile Glu Glu Arg Thr Ala Pro Thr Ala Leu Gly Ile Thr Leu Ser Ser
        340                 345                 350 tcc cca act tca aca cca gag ttg cgg gtt gat gct tct act cag aaa      1163
Ser Pro Thr Ser Thr Pro Glu Leu Arg Val Asp Ala Ser Thr Gln Lys
    355                 360                 365 ggt gaa gaa agt gag aca ttt gat gta gaa ctc act aaa aat gtc caa      1211
Gly Glu Glu Ser Glu Thr Phe Asp Val Glu Leu Thr Lys Asn Val Gln
370                 375                 380                 385 gga tta gga att acc att gct ggc tac att gga gat aaa aaa ttg gaa      1259
Gly Leu Gly Ile Thr Ile Ala Gly Tyr Ile Gly Asp Lys Lys Leu Glu
                390                 395                 400 cct tca gga atc ttt gta aag agc att aca aaa agc agt gcc gtt gag      1307
Pro Ser Gly Ile Phe Val Lys Ser Ile Thr Lys Ser Ser Ala Val Glu
            405                 410                 415 cat gat gga aga atc caa att gga gac caa att ata gca gta gat ggc      1355
His Asp Gly Arg Ile Gln Ile Gly Asp Gln Ile Ile Ala Val Asp Gly
        420                 425                 430 aca aac ctt cag ggt ttt act aat cag caa gca gta gag gta ttg cga      1403
Thr Asn Leu Gln Gly Phe Thr Asn Gln Gln Ala Val Glu Val Leu Arg
    435                 440                 445 cat aca gga caa act gtg ctc ctg aca cta atg agg aga gga atg aag      1451
His Thr Gly Gln Thr Val Leu Leu Thr Leu Met Arg Arg Gly Met Lys
450                 455                 460                 465
```

-continued

| | |
|---|---|
| cag gaa gcc gag ctc atg tca agg gaa gac gtc aca aaa gat gca gat<br>Gln Glu Ala Glu Leu Met Ser Arg Glu Asp Val Thr Lys Asp Ala Asp<br>470 475 480 | 1499 |
| ttg tct cct gtt aat gcc agc ata atc aaa gaa aat tat gaa aaa gat<br>Leu Ser Pro Val Asn Ala Ser Ile Ile Lys Glu Asn Tyr Glu Lys Asp<br>485 490 495 | 1547 |
| gaa gat ttt tta tct tcg acg aga aac acc aac ata tta cca act gaa<br>Glu Asp Phe Leu Ser Ser Thr Arg Asn Thr Asn Ile Leu Pro Thr Glu<br>500 505 510 | 1595 |
| gaa gaa ggg tat cca tta ctg tca gct gag ata gaa gaa ata gaa gat<br>Glu Glu Gly Tyr Pro Leu Leu Ser Ala Glu Ile Glu Glu Ile Glu Asp<br>515 520 525 | 1643 |
| gca caa aaa caa gaa gct gct ctg ctg aca aaa tgg caa agg att atg<br>Ala Gln Lys Gln Glu Ala Ala Leu Leu Thr Lys Trp Gln Arg Ile Met<br>530 535 540 545 | 1691 |
| gga att aac tat gaa ata gtg gtg gcc cat gtg agc aag ttt agt gag<br>Gly Ile Asn Tyr Glu Ile Val Val Ala His Val Ser Lys Phe Ser Glu<br>550 555 560 | 1739 |
| aac agt gga ttg ggg ata agc ctg gaa gcg aca gtg gga cat cat ttt<br>Asn Ser Gly Leu Gly Ile Ser Leu Glu Ala Thr Val Gly His His Phe<br>565 570 575 | 1787 |
| atc cga tct gtt cta cca gag ggt cct gtt gga cac agc ggg aag ctc<br>Ile Arg Ser Val Leu Pro Glu Gly Pro Val Gly His Ser Gly Lys Leu<br>580 585 590 | 1835 |
| ttc agt gga gac gag cta ttg gaa gta aat ggc ata act tta ctt ggg<br>Phe Ser Gly Asp Glu Leu Leu Glu Val Asn Gly Ile Thr Leu Leu Gly<br>595 600 605 | 1883 |
| gaa aat cac caa gat gtg gtg aat atc tta aaa gaa ctg cct ata gaa<br>Glu Asn His Gln Asp Val Val Asn Ile Leu Lys Glu Leu Pro Ile Glu<br>610 615 620 625 | 1931 |
| gtg aca atg gtg tgc tgt cgt cga act gtg cca ccc acc acc caa tca<br>Val Thr Met Val Cys Cys Arg Arg Thr Val Pro Pro Thr Thr Gln Ser<br>630 635 640 | 1979 |
| gaa ttg gat agc ctg gac tta tgt gat att gag cta aca gaa aag cct<br>Glu Leu Asp Ser Leu Asp Leu Cys Asp Ile Glu Leu Thr Glu Lys Pro<br>645 650 655 | 2027 |
| cac gta gat cta ggt gag ttc atc ggg tca tca gag aca gag gat cca<br>His Val Asp Leu Gly Glu Phe Ile Gly Ser Ser Glu Thr Glu Asp Pro<br>660 665 670 | 2075 |
| gtg ctg gcg atg act gat gcg ggt cag agt aca gaa gag gtt caa gca<br>Val Leu Ala Met Thr Asp Ala Gly Gln Ser Thr Glu Glu Val Gln Ala<br>675 680 685 | 2123 |
| cct ttg gcc atg tgg gag gct ggc att cag cac ata gag ctg gag aaa<br>Pro Leu Ala Met Trp Glu Ala Gly Ile Gln His Ile Glu Leu Glu Lys<br>690 695 700 705 | 2171 |
| ggg agc aaa gga ctt ggt ttt agc att tta gat tat cag gat cca att<br>Gly Ser Lys Gly Leu Gly Phe Ser Ile Leu Asp Tyr Gln Asp Pro Ile<br>710 715 720 | 2219 |
| gat cca gca agc act gtg att ata att cgt tct ttg gtg cct ggc ggc<br>Asp Pro Ala Ser Thr Val Ile Ile Ile Arg Ser Leu Val Pro Gly Gly<br>725 730 735 | 2267 |
| att gct gaa aag gat gga cga ctt ctt cct ggt gac cga ctc atg ttt<br>Ile Ala Glu Lys Asp Gly Arg Leu Leu Pro Gly Asp Arg Leu Met Phe<br>740 745 750 | 2315 |
| gta aac gat gtt aac ttg gaa aac agc agt ctt gag gaa gct gta gaa<br>Val Asn Asp Val Asn Leu Glu Asn Ser Ser Leu Glu Glu Ala Val Glu<br>755 760 765 | 2363 |
| gca ctg aag gga gca ccg tca ggg act gtg aga ata gga gtt gct aag<br>Ala Leu Lys Gly Ala Pro Ser Gly Thr Val Arg Ile Gly Val Ala Lys<br>770 775 780 785 | 2411 |

-continued

| | | |
|---|---|---|
| cct tta ccc ctt tca cca gaa gaa ggt tat gtt tct gct aag gag gat<br>Pro Leu Pro Leu Ser Pro Glu Glu Gly Tyr Val Ser Ala Lys Glu Asp<br>790 795 800 | 2459 | |
| tcc ttt ctc tac cca cca cac tcc tgt gag gaa gca ggg ctg gct gac<br>Ser Phe Leu Tyr Pro Pro His Ser Cys Glu Glu Ala Gly Leu Ala Asp<br>805 810 815 | 2507 | |
| aaa ccc ctc ttc agg gct gac ttg gct ctg gtg ggc aca aat gat gct<br>Lys Pro Leu Phe Arg Ala Asp Leu Ala Leu Val Gly Thr Asn Asp Ala<br>820 825 830 | 2555 | |
| gac tta gta gat gaa tcc aca ttt gag tct cca tac tct cct gaa aat<br>Asp Leu Val Asp Glu Ser Thr Phe Glu Ser Pro Tyr Ser Pro Glu Asn<br>835 840 845 | 2603 | |
| gac agc atc tac tct act caa gcc tct att tta tct ctt cat ggc agt<br>Asp Ser Ile Tyr Ser Thr Gln Ala Ser Ile Leu Ser Leu His Gly Ser<br>850 855 860 865 | 2651 | |
| tct tgt ggt gat ggc ctg aac tat ggt tct tcc ctt cca tca tct cct<br>Ser Cys Gly Asp Gly Leu Asn Tyr Gly Ser Ser Leu Pro Ser Ser Pro<br>870 875 880 | 2699 | |
| cct aag gat gtt att gaa aat tct tgt gat cca gta ctt gat ctg cat<br>Pro Lys Asp Val Ile Glu Asn Ser Cys Asp Pro Val Leu Asp Leu His<br>885 890 895 | 2747 | |
| atg tct ctg gag gaa cta tat acc cag aat ctc ctg caa aga cag gat<br>Met Ser Leu Glu Glu Leu Tyr Thr Gln Asn Leu Leu Gln Arg Gln Asp<br>900 905 910 | 2795 | |
| gag aat aca cct tcg gtg gac ata agt atg ggg cct gct tct ggc ttt<br>Glu Asn Thr Pro Ser Val Asp Ile Ser Met Gly Pro Ala Ser Gly Phe<br>915 920 925 | 2843 | |
| act ata aat gac tac aca cct gca aat gct att gaa caa caa tat gaa<br>Thr Ile Asn Asp Tyr Thr Pro Ala Asn Ala Ile Glu Gln Gln Tyr Glu<br>930 935 940 945 | 2891 | |
| tgt gaa aac aca ata gtg tgg act gaa tct cat tta cca agt gaa gtt<br>Cys Glu Asn Thr Ile Val Trp Thr Glu Ser His Leu Pro Ser Glu Val<br>950 955 960 | 2939 | |
| ata tca agt gca gaa ctt cct tct gtg cta ccc gat tca gct gga aag<br>Ile Ser Ser Ala Glu Leu Pro Ser Val Leu Pro Asp Ser Ala Gly Lys<br>965 970 975 | 2987 | |
| ggc tct gag tac ctg ctt gaa cag agc tcc ctg gcc tgt aat gct gag<br>Gly Ser Glu Tyr Leu Leu Glu Gln Ser Ser Leu Ala Cys Asn Ala Glu<br>980 985 990 | 3035 | |
| tgt gtc atg ctt caa aat gta tct aaa gaa tct ttt gaa agg act att<br>Cys Val Met Leu Gln Asn Val Ser Lys Glu Ser Phe Glu Arg Thr Ile<br>995 1000 1005 | 3083 | |
| aat ata gca aaa ggc aat tct agc cta gga atg aca gtt agt gct aat<br>Asn Ile Ala Lys Gly Asn Ser Ser Leu Gly Met Thr Val Ser Ala Asn<br>1010 1015 1020 1025 | 3131 | |
| aaa gat ggc ttg ggg atg atc gtt cga agc att att cat gga ggt gcc<br>Lys Asp Gly Leu Gly Met Ile Val Arg Ser Ile Ile His Gly Gly Ala<br>1030 1035 1040 | 3179 | |
| att agt cga gat ggc cgg att gcc att ggg gac tgc atc ttg tcc att<br>Ile Ser Arg Asp Gly Arg Ile Ala Ile Gly Asp Cys Ile Leu Ser Ile<br>1045 1050 1055 | 3227 | |
| aat gaa gag tct acc atc agt gta acc aat gcc cag gca cga gct atg<br>Asn Glu Glu Ser Thr Ile Ser Val Thr Asn Ala Gln Ala Arg Ala Met<br>1060 1065 1070 | 3275 | |
| ttg aga aga cat tct ctc att ggc cct gac ata aaa att act tat gtg<br>Leu Arg Arg His Ser Leu Ile Gly Pro Asp Ile Lys Ile Thr Tyr Val<br>1075 1080 1085 | 3323 | |
| cct gca gaa cat ttg gaa gag ttc aaa ata agc ttg gga caa caa tct<br>Pro Ala Glu His Leu Glu Glu Phe Lys Ile Ser Leu Gly Gln Gln Ser<br>1090 1095 1100 1105 | 3371 | |

| | |
|---|---|
| gga aga gta atg gca ctg gat att ttt tct tca tac act ggc aga gac<br>Gly Arg Val Met Ala Leu Asp Ile Phe Ser Ser Tyr Thr Gly Arg Asp<br>          1110                   1115                  1120 | 3419 |
| att cca gaa tta cca gag cga gaa gag gga gag ggt gaa gaa agc gaa<br>Ile Pro Glu Leu Pro Glu Arg Glu Glu Gly Glu Gly Glu Glu Ser Glu<br>        1125                   1130                  1135 | 3467 |
| ctt caa aac aca gca tat agc aat tgg aat cag ccc agg cgg gtg gaa<br>Leu Gln Asn Thr Ala Tyr Ser Asn Trp Asn Gln Pro Arg Arg Val Glu<br>1140                  1145                  1150 | 3515 |
| ctc tgg aga gaa cca agc aaa tcc tta ggc atc agc att gtt ggt gga<br>Leu Trp Arg Glu Pro Ser Lys Ser Leu Gly Ile Ser Ile Val Gly Gly<br>        1155                   1160                  1165 | 3563 |
| cga ggg atg ggg agt cgg cta agc aat gga gaa gtg atg agg ggc att<br>Arg Gly Met Gly Ser Arg Leu Ser Asn Gly Glu Val Met Arg Gly Ile<br>1170                  1175                  1180                  1185 | 3611 |
| ttc atc aaa cat gtt ctg gaa gat agt cca gct ggc aaa aat gga acc<br>Phe Ile Lys His Val Leu Glu Asp Ser Pro Ala Gly Lys Asn Gly Thr<br>          1190                   1195                  1200 | 3659 |
| ttg aaa cct gga gat aga atc gta gag gtg gat gga atg gac ctc aga<br>Leu Lys Pro Gly Asp Arg Ile Val Glu Val Asp Gly Met Asp Leu Arg<br>        1205                   1210                  1215 | 3707 |
| gat gca agc cat gaa caa gct gtg gaa gcc att cgg aaa gca ggc aac<br>Asp Ala Ser His Glu Gln Ala Val Glu Ala Ile Arg Lys Ala Gly Asn<br>1220                  1225                  1230 | 3755 |
| cct gta gtc ttt atg gta cag agc att ata aac aga cca agg gca ccc<br>Pro Val Val Phe Met Val Gln Ser Ile Ile Asn Arg Pro Arg Ala Pro<br>          1235                   1240                  1245 | 3803 |
| agt cag tca gag tca gag cca gag aag gct cca ttg tgc agt gtg ccc<br>Ser Gln Ser Glu Ser Glu Pro Glu Lys Ala Pro Leu Cys Ser Val Pro<br>1250                  1255                  1260                  1265 | 3851 |
| cca ccc cct cct tca gcc ttt gcc gaa atg ggt agt gat cac aca cag<br>Pro Pro Pro Pro Ser Ala Phe Ala Glu Met Gly Ser Asp His Thr Gln<br>          1270                   1275                  1280 | 3899 |
| tca tct gca agc aaa atc tca caa gat gtg gac aaa gag gat gag ttt<br>Ser Ser Ala Ser Lys Ile Ser Gln Asp Val Asp Lys Glu Asp Glu Phe<br>        1285                   1290                  1295 | 3947 |
| ggt tac agc tgg aaa aat atc aga gag cgt tat gga acc cta aca ggc<br>Gly Tyr Ser Trp Lys Asn Ile Arg Glu Arg Tyr Gly Thr Leu Thr Gly<br>1300                  1305                  1310 | 3995 |
| gag ctg cat atg att gaa ctg gag aaa ggt cat agt ggt ttg ggc cta<br>Glu Leu His Met Ile Glu Leu Glu Lys Gly His Ser Gly Leu Gly Leu<br>          1315                   1320                  1325 | 4043 |
| agt ctt gct ggg aac aaa gac cga tcc agg atg agt gtc ttc ata gtg<br>Ser Leu Ala Gly Asn Lys Asp Arg Ser Arg Met Ser Val Phe Ile Val<br>1330                  1335                  1340                  1345 | 4091 |
| ggg att gat cca aat gga gct gca gga aaa gat ggt cga ttg caa att<br>Gly Ile Asp Pro Asn Gly Ala Ala Gly Lys Asp Gly Arg Leu Gln Ile<br>          1350                   1355                  1360 | 4139 |
| gca gat gag ctt cta gag atc aat ggt cag att tta tat gga aga agt<br>Ala Asp Glu Leu Leu Glu Ile Asn Gly Gln Ile Leu Tyr Gly Arg Ser<br>        1365                   1370                  1375 | 4187 |
| cat cag aat gcc tca tca atc att aaa tgt gcc cct tct aaa gtg aaa<br>His Gln Asn Ala Ser Ser Ile Ile Lys Cys Ala Pro Ser Lys Val Lys<br>1380                  1385                  1390 | 4235 |
| ata att ttt atc aga aat aaa gat gca gtg aat cag atg gcc gta tgt<br>Ile Ile Phe Ile Arg Asn Lys Asp Ala Val Asn Gln Met Ala Val Cys<br>          1395                   1400                  1405 | 4283 |
| cct gga aat gca gta gaa cct ttg cct tct aac tca gaa aat ctt caa<br>Pro Gly Asn Ala Val Glu Pro Leu Pro Ser Asn Ser Glu Asn Leu Gln<br>1410                  1415                  1420                  1425 | 4331 |

```
aat aag gag aca gag cca act gtt act act tct gat gca gct gtg gac      4379
Asn Lys Glu Thr Glu Pro Thr Val Thr Thr Ser Asp Ala Ala Val Asp
        1430                1435                1440 ctc agt tca ttt aaa aat gtg caa cat ctg gag ctt ccc aag gat cag      4427
Leu Ser Ser Phe Lys Asn Val Gln His Leu Glu Leu Pro Lys Asp Gln
            1445                1450                1455 ggg ggt ttg ggt att gct atc agc gaa gaa gat aca ctc agt gga gtc      4475
Gly Gly Leu Gly Ile Ala Ile Ser Glu Glu Asp Thr Leu Ser Gly Val
        1460                1465                1470 atc ata aag agc tta aca gag cat ggg gta gca gcc acg gat gga cga      4523
Ile Ile Lys Ser Leu Thr Glu His Gly Val Ala Ala Thr Asp Gly Arg
    1475                1480                1485 ctc aaa gtc gga gat cag ata ctg gct gta gat gat gaa att gtt gtt      4571
Leu Lys Val Gly Asp Gln Ile Leu Ala Val Asp Asp Glu Ile Val Val
1490                1495                1500                1505 ggt tac cct att gaa aag ttt att agc ctt ctg aag aca gca aag atg      4619
Gly Tyr Pro Ile Glu Lys Phe Ile Ser Leu Leu Lys Thr Ala Lys Met
        1510                1515                1520 aca gta aaa ctt acc atc cat gct gag aat cca gat tcc cag gct gtt      4667
Thr Val Lys Leu Thr Ile His Ala Glu Asn Pro Asp Ser Gln Ala Val
            1525                1530                1535 cct tca gca gct ggt gca gcc agt gga gaa aaa aag aac agc tcc cag      4715
Pro Ser Ala Ala Gly Ala Ala Ser Gly Glu Lys Lys Asn Ser Ser Gln
        1540                1545                1550 tct ctg atg gtc cca cag tct ggc tcc cca gaa ccg gag tcc atc cga      4763
Ser Leu Met Val Pro Gln Ser Gly Ser Pro Glu Pro Glu Ser Ile Arg
    1555                1560                1565 aat aca agc aga tca tca aca cca gca att ttt gct tct gat cct gca      4811
Asn Thr Ser Arg Ser Ser Thr Pro Ala Ile Phe Ala Ser Asp Pro Ala
1570                1575                1580                1585 acc tgc ccc att atc cct ggc tgc gaa aca acc atc gag att tcc aaa      4859
Thr Cys Pro Ile Ile Pro Gly Cys Glu Thr Thr Ile Glu Ile Ser Lys
        1590                1595                1600 ggg cga aca ggg ctg ggc ctg agc atc gtt ggg ggt tca gac acg ctg      4907
Gly Arg Thr Gly Leu Gly Leu Ser Ile Val Gly Gly Ser Asp Thr Leu
            1605                1610                1615 ctg ggt gcc att att atc cat gaa gtt tat gaa gaa gga gca gca tgt      4955
Leu Gly Ala Ile Ile Ile His Glu Val Tyr Glu Glu Gly Ala Ala Cys
        1620                1625                1630 aaa gat gga aga ctc tgg gct gga gat cag atc tta gag gtg aat gga      5003
Lys Asp Gly Arg Leu Trp Ala Gly Asp Gln Ile Leu Glu Val Asn Gly
    1635                1640                1645 att gac ttg aga aag gcc aca cat gat gaa gca atc aat gtc ctg aga      5051
Ile Asp Leu Arg Lys Ala Thr His Asp Glu Ala Ile Asn Val Leu Arg
1650                1655                1660                1665 cag acg cca cag aga gtg cgc ctg aca ctc tac aga gat gag gcc cca      5099
Gln Thr Pro Gln Arg Val Arg Leu Thr Leu Tyr Arg Asp Glu Ala Pro
        1670                1675                1680 tac aaa gag gag gaa gtg tgt gac acc ctc act att gag ctg cag aag      5147
Tyr Lys Glu Glu Glu Val Cys Asp Thr Leu Thr Ile Glu Leu Gln Lys
            1685                1690                1695 aag ccg gga aaa ggc cta gga tta agt att gtt ggt aaa aga aac gat      5195
Lys Pro Gly Lys Gly Leu Gly Leu Ser Ile Val Gly Lys Arg Asn Asp
        1700                1705                1710 act gga gta ttt gtg tca gac att gtc aaa gga gga att gca gat gcc      5243
Thr Gly Val Phe Val Ser Asp Ile Val Lys Gly Gly Ile Ala Asp Ala
    1715                1720                1725 gat gga aga ctg atg cag gga gac cag ata tta atg gtg aat ggg gaa      5291
Asp Gly Arg Leu Met Gln Gly Asp Gln Ile Leu Met Val Asn Gly Glu
1730                1735                1740                1745
```

```
gac gtt cgt aat gcc acc caa gaa gcg gtt gcc gct ttg cta aag tgt      5339
Asp Val Arg Asn Ala Thr Gln Glu Ala Val Ala Ala Leu Leu Lys Cys
            1750                1755                1760 tcc cta ggc aca gta acc ttg gaa gtt gga aga atc aaa gct ggt cca      5387
Ser Leu Gly Thr Val Thr Leu Glu Val Gly Arg Ile Lys Ala Gly Pro
        1765                1770                1775 ttc cat tca gag agg agg cca tct caa agc agc cag gtg agt gaa ggc      5435
Phe His Ser Glu Arg Arg Pro Ser Gln Ser Ser Gln Val Ser Glu Gly
        1780                1785                1790 agc ctg tca tct ttc act ttt cca ctc tct gga tcc agt aca tct gag      5483
Ser Leu Ser Ser Phe Thr Phe Pro Leu Ser Gly Ser Ser Thr Ser Glu
    1795                1800                1805 tca ctg gaa agt agc tca aag aag aat gca ttg gca tct gaa ata cag      5531
Ser Leu Glu Ser Ser Ser Lys Lys Asn Ala Leu Ala Ser Glu Ile Gln
1810                1815                1820                1825 gga tta aga aca gtc gaa atg aaa aag ggc cct act gac tca ctg gga      5579
Gly Leu Arg Thr Val Glu Met Lys Lys Gly Pro Thr Asp Ser Leu Gly
            1830                1835                1840 atc agc atc gct gga gga gta ggc agc cca ctt ggt gat gtg cct ata      5627
Ile Ser Ile Ala Gly Gly Val Gly Ser Pro Leu Gly Asp Val Pro Ile
        1845                1850                1855 ttt att gca atg atg cac cca act gga gtt gca gca cag acc caa aaa      5675
Phe Ile Ala Met Met His Pro Thr Gly Val Ala Ala Gln Thr Gln Lys
        1860                1865                1870 ctc aga gtt ggg gat agg att gtc acc atc tgt ggc aca tcc act gag      5723
Leu Arg Val Gly Asp Arg Ile Val Thr Ile Cys Gly Thr Ser Thr Glu
    1875                1880                1885 ggc atg act cac acc caa gca gtt aac cta ctg aaa aat gca tct ggc      5771
Gly Met Thr His Thr Gln Ala Val Asn Leu Leu Lys Asn Ala Ser Gly
1890                1895                1900                1905 tcc att gaa atg cag gtg gtt gct gga gga gac gtg agt gtg gtc aca      5819
Ser Ile Glu Met Gln Val Val Ala Gly Gly Asp Val Ser Val Val Thr
            1910                1915                1920 ggt cat cag cag gag cct gca agt tcc agt ctt tct ttc act ggg ctg      5867
Gly His Gln Gln Glu Pro Ala Ser Ser Ser Leu Ser Phe Thr Gly Leu
        1925                1930                1935 acg tca agc agt ata ttt cag gat gat tta gga cct cct caa tgt aag      5915
Thr Ser Ser Ser Ile Phe Gln Asp Asp Leu Gly Pro Pro Gln Cys Lys
        1940                1945                1950 tct att aca cta gag cga gga cca gat ggc tta ggc ttc agt ata gtt      5963
Ser Ile Thr Leu Glu Arg Gly Pro Asp Gly Leu Gly Phe Ser Ile Val
    1955                1960                1965 gga gga tat ggc agc cct cat gga gac tta ccc att tat gtt aaa aca      6011
Gly Gly Tyr Gly Ser Pro His Gly Asp Leu Pro Ile Tyr Val Lys Thr
1970                1975                1980                1985 gtg ttt gca aag gga gca gcc tct gaa gac gga cgt ctg aaa agg ggc      6059
Val Phe Ala Lys Gly Ala Ala Ser Glu Asp Gly Arg Leu Lys Arg Gly
            1990                1995                2000 gat cag atc att gct gtc aat ggg cag agt cta gaa gga gtc acc cat      6107
Asp Gln Ile Ile Ala Val Asn Gly Gln Ser Leu Glu Gly Val Thr His
        2005                2010                2015 gaa gaa gct gtt gcc atc ctt aaa cgg aca aaa ggc act gtc act ttg      6155
Glu Glu Ala Val Ala Ile Leu Lys Arg Thr Lys Gly Thr Val Thr Leu
    2020                2025                2030 atg gtt ctc tct tgaattggct gccagaattg aaccaaccca acccctagct          6207
Met Val Leu Ser
    2035 cacctcctac tgtaaagaga atgcactggt cctgacaatt tttatgctgt gttcagccgg    6267 gtcttcaaaa ctgtaggggg gaaataacac ttaagtttct ttttctcatc tagaaatgct    6327
```

-continued

```
ttccttactg acaacctaac atcatttttc ttttcttctt gcattttgtg aacttaaaga      6387
gaaggaatat tgtgtaggt gaatctcgtt tttatttgtg gagatatcta atgttttgta      6447
gtcacatggg caagaattat tacatgctaa gctggttagt ataaagaaag ataattctaa      6507
agctaaccaa agaaaatggc ttcagtaaat taggatgaaa aatgaaaata taaaataaag      6567
aagaaaatct cggggagttt aaaaaaaatg cctcaatttg gcaatctacc tcctctcccc      6627
accccaaact aaaaaaagaa aaaaggtttt tctaatgaaa atctttaaaa atactgtcag      6687
tattttaaaa ttttcaacag tattataaaa acattgcatc tccccacctc taatatgcat      6747
atatattttt cctgctaaaa ttggtttcta caattgagta aatggcaaat acatgaagca      6807
atgtccctaa atttataaa gaaattatat ttaatgcaca tttcaattt cattcttatt      6867 tttgaccttt tataaaatat tttcatgttg ctataagtaa atgatgatgc cacccccatgt      6927 tgactatggt ttttctagaa agcaactatg ctgctaacca tagaggaaca tagaagggtt      6987
ccagaatctt tagtgctggt tttaacaacc gatgcaacat taaaaatgtg ttagtgtgct      7047
gtgcaattgg ttttcaattc atattaatct taatgacaga gaacaatgtg ttactaatta      7107
ttttggttgt atgccattag taaattgata gaaaaattaa ggggattaac ataacttcat      7167
ttcattgcct tatattaaca tcttataata caatagttta agactaaggg aaacagatgg      7227
agctgtttat tgagacaact ggtgaggaat tatcatgtgt tcattcccat tttagagcgt      7287
gaaactccta cattagaata tataaagtca ctttaaatat ctatatttgt aacagaagta      7347
gtgtacagat attttattac agcattttg tgtaaatgca gaattaaagt gaataaataa      7407
gaattttcag tggtgcaaaa aaaa                                            7431
```

<210> SEQ ID NO 3
<211> LENGTH: 2037
<212> TYPE: PRT
<213> ORGANISM: Homo sapiens

<400> SEQUENCE: 3

```
Met Leu Glu Ala Ile Asp Lys Asn Arg Ala Leu His Ala Ala Glu Arg
  1               5                  10                  15

Leu Gln Thr Lys Leu Arg Glu Arg Gly Asp Val Ala Asn Glu Asp Lys
                 20                  25                  30

Leu Ser Leu Leu Lys Ser Val Leu Gln Ser Pro Leu Phe Ser Gln Ile
             35                  40                  45

Leu Ser Leu Gln Thr Ser Val Gln Gln Leu Lys Asp Gln Val Asn Ile
         50                  55                  60

Ala Thr Ser Ala Thr Ser Asn Ile Glu Tyr Ala His Val Pro His Leu
 65                  70                  75                  80

Ser Pro Ala Val Ile Pro Thr Leu Gln Asn Glu Ser Phe Leu Leu Ser
                 85                  90                  95

Pro Asn Asn Gly Asn Leu Glu Ala Leu Thr Gly Pro Gly Ile Pro His
                100                 105                 110

Ile Asn Gly Lys Pro Ala Cys Asp Glu Phe Asp Gln Leu Ile Lys Asn
            115                 120                 125

Met Ala Gln Gly Arg His Val Glu Val Phe Glu Leu Leu Lys Pro Pro
        130                 135                 140

Ser Gly Gly Leu Gly Phe Ser Val Val Gly Leu Arg Ser Glu Asn Arg
145                 150                 155                 160

Gly Glu Leu Gly Ile Phe Val Gln Glu Ile Gln Glu Gly Ser Val Ala
                165                 170                 175
```

-continued

His Arg Asp Gly Arg Leu Lys Glu Thr Asp Gln Ile Leu Ala Ile Asn
            180                 185                 190

Gly Gln Ala Leu Asp Gln Thr Ile Thr His Gln Gln Ala Ile Ser Ile
            195                 200                 205

Leu Gln Lys Ala Lys Asp Thr Val Gln Leu Val Ile Ala Arg Gly Ser
210                 215                 220

Leu Pro Gln Leu Val Ser Pro Ile Val Ser Arg Ser Pro Ser Ala Ala
225                 230                 235                 240

Ser Thr Ile Ser Ala His Ser Asn Pro Val His Trp Gln His Met Glu
            245                 250                 255

Thr Ile Glu Leu Val Asn Asp Gly Ser Gly Leu Gly Phe Gly Ile Ile
            260                 265                 270

Gly Gly Lys Ala Thr Gly Val Ile Val Lys Thr Ile Leu Pro Gly Gly
            275                 280                 285

Val Ala Asp Gln His Gly Arg Leu Cys Ser Gly Asp His Ile Leu Lys
            290                 295                 300

Ile Gly Asp Thr Asp Leu Ala Gly Met Ser Ser Glu Gln Val Ala Gln
305                 310                 315                 320

Val Leu Arg Gln Cys Gly Asn Arg Val Lys Leu Met Ile Ala Arg Gly
            325                 330                 335

Ala Ile Glu Glu Arg Thr Ala Pro Thr Ala Leu Gly Ile Thr Leu Ser
            340                 345                 350

Ser Ser Pro Thr Ser Thr Pro Glu Leu Arg Val Asp Ala Ser Thr Gln
            355                 360                 365

Lys Gly Glu Glu Ser Glu Thr Phe Asp Val Glu Leu Thr Lys Asn Val
            370                 375                 380

Gln Gly Leu Gly Ile Thr Ile Ala Gly Tyr Ile Gly Asp Lys Lys Leu
385                 390                 395                 400

Glu Pro Ser Gly Ile Phe Val Lys Ser Ile Thr Lys Ser Ser Ala Val
            405                 410                 415

Glu His Asp Gly Arg Ile Gln Ile Gly Asp Gln Ile Ile Ala Val Asp
            420                 425                 430

Gly Thr Asn Leu Gln Gly Phe Thr Asn Gln Gln Ala Val Glu Val Leu
            435                 440                 445

Arg His Thr Gly Gln Thr Val Leu Leu Thr Leu Met Arg Arg Gly Met
450                 455                 460

Lys Gln Glu Ala Glu Leu Met Ser Arg Glu Asp Val Thr Lys Asp Ala
465                 470                 475                 480

Asp Leu Ser Pro Val Asn Ala Ser Ile Ile Lys Glu Asn Tyr Glu Lys
            485                 490                 495

Asp Glu Asp Phe Leu Ser Ser Thr Arg Asn Thr Asn Ile Leu Pro Thr
            500                 505                 510

Glu Glu Glu Gly Tyr Pro Leu Leu Ser Ala Glu Ile Glu Glu Ile Glu
            515                 520                 525

Asp Ala Gln Lys Gln Glu Ala Ala Leu Leu Thr Lys Trp Gln Arg Ile
530                 535                 540

Met Gly Ile Asn Tyr Glu Ile Val Val Ala His Val Ser Lys Phe Ser
545                 550                 555                 560

Glu Asn Ser Gly Leu Gly Ile Ser Leu Glu Ala Thr Val Gly His His
            565                 570                 575

Phe Ile Arg Ser Val Leu Pro Glu Gly Pro Val Gly His Ser Gly Lys
            580                 585                 590

-continued

```
Leu Phe Ser Gly Asp Glu Leu Leu Glu Val Asn Gly Ile Thr Leu Leu
            595                 600                 605

Gly Glu Asn His Gln Asp Val Val Asn Ile Leu Lys Glu Leu Pro Ile
    610                 615                 620

Glu Val Thr Met Val Cys Cys Arg Arg Thr Val Pro Pro Thr Thr Gln
625                 630                 635                 640

Ser Glu Leu Asp Ser Leu Asp Leu Cys Asp Ile Glu Leu Thr Glu Lys
                645                 650                 655

Pro His Val Asp Leu Gly Glu Phe Ile Gly Ser Ser Glu Thr Glu Asp
            660                 665                 670

Pro Val Leu Ala Met Thr Asp Ala Gly Gln Ser Thr Glu Glu Val Gln
            675                 680                 685

Ala Pro Leu Ala Met Trp Glu Ala Gly Ile Gln His Ile Glu Leu Glu
            690                 695                 700

Lys Gly Ser Lys Gly Leu Gly Phe Ser Ile Leu Asp Tyr Gln Asp Pro
705                 710                 715                 720

Ile Asp Pro Ala Ser Thr Val Ile Ile Arg Ser Leu Val Pro Gly
                725                 730                 735

Gly Ile Ala Glu Lys Asp Gly Arg Leu Leu Pro Gly Asp Arg Leu Met
            740                 745                 750

Phe Val Asn Asp Val Asn Leu Glu Asn Ser Ser Leu Glu Glu Ala Val
            755                 760                 765

Glu Ala Leu Lys Gly Ala Pro Ser Gly Thr Val Arg Ile Gly Val Ala
770                 775                 780

Lys Pro Leu Pro Leu Ser Pro Glu Glu Gly Tyr Val Ser Ala Lys Glu
785                 790                 795                 800

Asp Ser Phe Leu Tyr Pro Pro His Ser Cys Glu Ala Gly Leu Ala
                805                 810                 815

Asp Lys Pro Leu Phe Arg Ala Asp Leu Ala Leu Val Gly Thr Asn Asp
            820                 825                 830

Ala Asp Leu Val Asp Glu Ser Thr Phe Glu Ser Pro Tyr Ser Pro Glu
            835                 840                 845

Asn Asp Ser Ile Tyr Ser Thr Gln Ala Ser Ile Leu Ser Leu His Gly
850                 855                 860

Ser Ser Cys Gly Asp Gly Leu Asn Tyr Gly Ser Ser Leu Pro Ser Ser
865                 870                 875                 880

Pro Pro Lys Asp Val Ile Glu Asn Ser Cys Asp Pro Val Leu Asp Leu
                885                 890                 895

His Met Ser Leu Glu Glu Leu Tyr Thr Gln Asn Leu Leu Gln Arg Gln
            900                 905                 910

Asp Glu Asn Thr Pro Ser Val Asp Ile Ser Met Gly Pro Ala Ser Gly
            915                 920                 925

Phe Thr Ile Asn Asp Tyr Thr Pro Ala Asn Ala Ile Glu Gln Gln Tyr
            930                 935                 940

Glu Cys Glu Asn Thr Ile Val Trp Thr Glu Ser His Leu Pro Ser Glu
945                 950                 955                 960

Val Ile Ser Ser Ala Glu Leu Pro Ser Val Leu Pro Asp Ser Ala Gly
                965                 970                 975

Lys Gly Ser Glu Tyr Leu Leu Glu Gln Ser Ser Leu Ala Cys Asn Ala
            980                 985                 990

Glu Cys Val Met Leu Gln Asn Val Ser Lys Glu Ser Phe Glu Arg Thr
            995                 1000                1005
```

-continued

Ile Asn Ile Ala Lys Gly Asn Ser Ser Leu Gly Met Thr Val Ser Ala
    1010            1015            1020

Asn Lys Asp Gly Leu Gly Met Ile Val Arg Ser Ile Ile His Gly Gly
1025            1030            1035            1040

Ala Ile Ser Arg Asp Gly Arg Ile Ala Ile Gly Asp Cys Ile Leu Ser
            1045            1050            1055

Ile Asn Glu Glu Ser Thr Ile Ser Val Thr Asn Ala Gln Ala Arg Ala
        1060            1065            1070

Met Leu Arg Arg His Ser Leu Ile Gly Pro Asp Ile Lys Ile Thr Tyr
    1075            1080            1085

Val Pro Ala Glu His Leu Glu Glu Phe Lys Ile Ser Leu Gly Gln Gln
    1090            1095            1100

Ser Gly Arg Val Met Ala Leu Asp Ile Phe Ser Ser Tyr Thr Gly Arg
1105            1110            1115            1120

Asp Ile Pro Glu Leu Pro Glu Arg Glu Glu Gly Glu Gly Glu Glu Ser
            1125            1130            1135

Glu Leu Gln Asn Thr Ala Tyr Ser Asn Trp Asn Gln Pro Arg Arg Val
        1140            1145            1150

Glu Leu Trp Arg Glu Pro Ser Lys Ser Leu Gly Ile Ser Ile Val Gly
    1155            1160            1165

Gly Arg Gly Met Gly Ser Arg Leu Ser Asn Gly Glu Val Met Arg Gly
    1170            1175            1180

Ile Phe Ile Lys His Val Leu Glu Asp Ser Pro Ala Gly Lys Asn Gly
1185            1190            1195            1200

Thr Leu Lys Pro Gly Asp Arg Ile Val Glu Val Asp Gly Met Asp Leu
            1205            1210            1215

Arg Asp Ala Ser His Glu Gln Ala Val Glu Ala Ile Arg Lys Ala Gly
        1220            1225            1230

Asn Pro Val Val Phe Met Val Gln Ser Ile Ile Asn Arg Pro Arg Ala
    1235            1240            1245

Pro Ser Gln Ser Glu Ser Glu Pro Glu Lys Ala Pro Leu Cys Ser Val
    1250            1255            1260

Pro Pro Pro Pro Pro Ser Ala Phe Ala Glu Met Gly Ser Asp His Thr
1265            1270            1275            1280

Gln Ser Ser Ala Ser Lys Ile Ser Gln Asp Val Asp Lys Glu Asp Glu
            1285            1290            1295

Phe Gly Tyr Ser Trp Lys Asn Ile Arg Glu Arg Tyr Gly Thr Leu Thr
        1300            1305            1310

Gly Glu Leu His Met Ile Glu Leu Glu Lys Gly His Ser Gly Leu Gly
    1315            1320            1325

Leu Ser Leu Ala Gly Asn Lys Asp Arg Ser Arg Met Ser Val Phe Ile
    1330            1335            1340

Val Gly Ile Asp Pro Asn Gly Ala Ala Gly Lys Asp Gly Arg Leu Gln
1345            1350            1355            1360

Ile Ala Asp Glu Leu Leu Glu Ile Asn Gly Gln Ile Leu Tyr Gly Arg
            1365            1370            1375

Ser His Gln Asn Ala Ser Ser Ile Ile Lys Cys Ala Pro Ser Lys Val
        1380            1385            1390

Lys Ile Ile Phe Ile Arg Asn Lys Asp Ala Val Asn Gln Met Ala Val
    1395            1400            1405

Cys Pro Gly Asn Ala Val Glu Pro Leu Pro Ser Asn Ser Glu Asn Leu
    1410            1415            1420

-continued

```
Gln Asn Lys Glu Thr Glu Pro Thr Val Thr Thr Ser Asp Ala Ala Val
1425                1430                1435                1440

Asp Leu Ser Ser Phe Lys Asn Val Gln His Leu Glu Leu Pro Lys Asp
                1445                1450                1455

Gln Gly Gly Leu Gly Ile Ala Ile Ser Glu Asp Thr Leu Ser Gly
            1460                1465                1470

Val Ile Ile Lys Ser Leu Thr Glu His Gly Val Ala Ala Thr Asp Gly
1475                1480                1485

Arg Leu Lys Val Gly Asp Gln Ile Leu Ala Val Asp Asp Glu Ile Val
        1490                1495                1500

Val Gly Tyr Pro Ile Glu Lys Phe Ile Ser Leu Leu Lys Thr Ala Lys
1505                1510                1515                1520

Met Thr Val Lys Leu Thr Ile His Ala Glu Asn Pro Asp Ser Gln Ala
            1525                1530                1535

Val Pro Ser Ala Ala Gly Ala Ala Ser Gly Glu Lys Lys Asn Ser Ser
            1540                1545                1550

Gln Ser Leu Met Val Pro Gln Ser Gly Ser Pro Glu Pro Glu Ser Ile
        1555                1560                1565

Arg Asn Thr Ser Arg Ser Ser Thr Pro Ala Ile Phe Ala Ser Asp Pro
    1570                1575                1580

Ala Thr Cys Pro Ile Ile Pro Gly Cys Glu Thr Thr Ile Glu Ile Ser
1585                1590                1595                1600

Lys Gly Arg Thr Gly Leu Gly Leu Ser Ile Val Gly Gly Ser Asp Thr
            1605                1610                1615

Leu Leu Gly Ala Ile Ile Ile His Glu Val Tyr Glu Glu Gly Ala Ala
        1620                1625                1630

Cys Lys Asp Gly Arg Leu Trp Ala Gly Asp Gln Ile Leu Glu Val Asn
    1635                1640                1645

Gly Ile Asp Leu Arg Lys Ala Thr His Asp Glu Ala Ile Asn Val Leu
    1650                1655                1660

Arg Gln Thr Pro Gln Arg Val Arg Leu Thr Leu Tyr Arg Asp Glu Ala
1665                1670                1675                1680

Pro Tyr Lys Glu Glu Val Cys Asp Thr Leu Thr Ile Glu Leu Gln
            1685                1690                1695

Lys Lys Pro Gly Lys Gly Leu Gly Leu Ser Ile Val Gly Lys Arg Asn
        1700                1705                1710

Asp Thr Gly Val Phe Val Ser Asp Ile Val Lys Gly Gly Ile Ala Asp
        1715                1720                1725

Ala Asp Gly Arg Leu Met Gln Gly Asp Gln Ile Leu Met Val Asn Gly
    1730                1735                1740

Glu Asp Val Arg Asn Ala Thr Gln Glu Ala Val Ala Ala Leu Leu Lys
1745                1750                1755                1760

Cys Ser Leu Gly Thr Val Thr Leu Glu Val Gly Arg Ile Lys Ala Gly
            1765                1770                1775

Pro Phe His Ser Glu Arg Arg Pro Ser Gln Ser Ser Gln Val Ser Glu
        1780                1785                1790

Gly Ser Leu Ser Ser Phe Thr Phe Pro Leu Ser Gly Ser Ser Thr Ser
        1795                1800                1805

Glu Ser Leu Glu Ser Ser Ser Lys Lys Asn Ala Leu Ala Ser Glu Ile
        1810                1815                1820

Gln Gly Leu Arg Thr Val Glu Met Lys Lys Gly Pro Thr Asp Ser Leu
1825                1830                1835                1840
```

```
Gly Ile Ser Ile Ala Gly Gly Val Gly Ser Pro Leu Gly Asp Val Pro
            1845                1850                1855

Ile Phe Ile Ala Met Met His Pro Thr Gly Val Ala Ala Gln Thr Gln
        1860                1865                1870

Lys Leu Arg Val Gly Asp Arg Ile Val Thr Ile Cys Gly Thr Ser Thr
        1875                1880                1885

Glu Gly Met Thr His Thr Gln Ala Val Asn Leu Leu Lys Asn Ala Ser
        1890                1895            1900

Gly Ser Ile Glu Met Gln Val Val Ala Gly Asp Val Ser Val Val
1905            1910                1915                1920

Thr Gly His Gln Gln Glu Pro Ala Ser Ser Ser Leu Ser Phe Thr Gly
            1925                1930                1935

Leu Thr Ser Ser Ser Ile Phe Gln Asp Asp Leu Gly Pro Pro Gln Cys
            1940                1945                1950

Lys Ser Ile Thr Leu Glu Arg Gly Pro Asp Gly Leu Gly Phe Ser Ile
            1955                1960                1965

Val Gly Gly Tyr Gly Ser Pro His Gly Asp Leu Pro Ile Tyr Val Lys
        1970                1975                1980

Thr Val Phe Ala Lys Gly Ala Ala Ser Glu Asp Gly Arg Leu Lys Arg
1985            1990                1995                2000

Gly Asp Gln Ile Ile Ala Val Asn Gly Gln Ser Leu Glu Gly Val Thr
            2005                2010                2015

His Glu Glu Ala Val Ala Ile Leu Lys Arg Thr Lys Gly Thr Val Thr
            2020                2025                2030

Leu Met Val Leu Ser
        2035

<210> SEQ ID NO 4
<211> LENGTH: 15
<212> TYPE: PRT
<213> ORGANISM: Homo sapiens

<400> SEQUENCE: 4

Asn Glu Pro Phe Asp Glu Asp Gln His Thr Gln Ile Thr Lys Val
 1               5                  10                  15

<210> SEQ ID NO 5
<211> LENGTH: 21
<212> TYPE: DNA
<213> ORGANISM: Homo sapiens

<400> SEQUENCE: 5
agacagcaaa gatgacagta a                                              21

<210> SEQ ID NO 6
<211> LENGTH: 20
<212> TYPE: DNA
<213> ORGANISM: Homo sapiens

<400> SEQUENCE: 6
cttcctcctc tttgtatggg                                                20

<210> SEQ ID NO 7
<211> LENGTH: 21
<212> TYPE: DNA
<213> ORGANISM: Homo sapiens

<400> SEQUENCE: 7
gcttttgccg aaatgggtag t                                              21
```

```
<210> SEQ ID NO 8
<211> LENGTH: 21
<212> TYPE: DNA
<213> ORGANISM: Homo sapiens

<400> SEQUENCE: 8
gatcggtctt tgttcccagc a                                              21

<210> SEQ ID NO 9
<211> LENGTH: 19
<212> TYPE: DNA
<213> ORGANISM: Homo sapiens

<400> SEQUENCE: 9
tgtgagcaag tttagtgag                                                 19

<210> SEQ ID NO 10
<211> LENGTH: 19
<212> TYPE: DNA
<213> ORGANISM: Homo sapiens

<400> SEQUENCE: 10
ggtgattttc cccaagtaa                                                 19

<210> SEQ ID NO 11
<211> LENGTH: 16
<212> TYPE: PRT
<213> ORGANISM: Homo sapiens

<400> SEQUENCE: 11

Ser Gly Ser Gly Ile Leu Ala Pro Pro Val Pro Pro Arg Asn Thr Arg
 1               5                  10                  15

<210> SEQ ID NO 12
<211> LENGTH: 16
<212> TYPE: PRT
<213> ORGANISM: Homo sapiens

<400> SEQUENCE: 12

Glu Asn Glu Pro Phe Asp Glu Asp Gln His Thr Gln Ile Thr Lys Val
 1               5                  10                  15

<210> SEQ ID NO 13
<211> LENGTH: 22
<212> TYPE: DNA
<213> ORGANISM: Homo sapiens

<400> SEQUENCE: 13
gccaccgcgg gattaagttt ct                                             22

<210> SEQ ID NO 14
<211> LENGTH: 23
<212> TYPE: DNA
<213> ORGANISM: Homo sapiens

<400> SEQUENCE: 14
tgtagccagc aatggtaatt cct                                            23

<210> SEQ ID NO 15
<211> LENGTH: 41
<212> TYPE: DNA
<213> ORGANISM: Homo sapiens
```

-continued

```
<400> SEQUENCE: 15
gttttcccag tcacgacggt tccatttta ttgctgttaa t                   41

<210> SEQ ID NO 16
<211> LENGTH: 43
<212> TYPE: DNA
<213> ORGANISM: Homo sapiens

<400> SEQUENCE: 16
aggaaacagc tatgaccatg gggataataa aaacgattca ggg                43

<210> SEQ ID NO 17
<211> LENGTH: 39
<212> TYPE: DNA
<213> ORGANISM: Homo sapiens

<400> SEQUENCE: 17
gttttcccag tcacgacgtt gaatatgccc acgttcctc                     39

<210> SEQ ID NO 18
<211> LENGTH: 42
<212> TYPE: DNA
<213> ORGANISM: Homo sapiens

<400> SEQUENCE: 18
aggaaacagc tatgaccatt ctttcaatct tccatctcta tg                 42

<210> SEQ ID NO 19
<211> LENGTH: 39
<212> TYPE: DNA
<213> ORGANISM: Homo sapiens

<400> SEQUENCE: 19
gttttcccag tcacgacgtt gaatatgccc acgttcctc                     39

<210> SEQ ID NO 20
<211> LENGTH: 41
<212> TYPE: DNA
<213> ORGANISM: Homo sapiens

<400> SEQUENCE: 20
aggaaacagc tatgaccatc aaaccagatc catcattcac c                  41

<210> SEQ ID NO 21
<211> LENGTH: 40
<212> TYPE: DNA
<213> ORGANISM: Homo sapiens

<400> SEQUENCE: 21
gttttcccag tcacgacggc acaatttcag ctcactctaa                    40

<210> SEQ ID NO 22
<211> LENGTH: 39
<212> TYPE: DNA
<213> ORGANISM: Homo sapiens

<400> SEQUENCE: 22
aggaaacagc tatgaccatg gatgaggaga gggtgatgc                     39

<210> SEQ ID NO 23
<211> LENGTH: 22
<212> TYPE: DNA
<213> ORGANISM: Homo sapiens
```

<400> SEQUENCE: 23
tctagcagga atgagcagtg ag                                          22

<210> SEQ ID NO 24
<211> LENGTH: 24
<212> TYPE: DNA
<213> ORGANISM: Homo sapiens

<400> SEQUENCE: 24
gatcctgata atctaaaatg ctaa                                        24

<210> SEQ ID NO 25
<211> LENGTH: 40
<212> TYPE: DNA
<213> ORGANISM: Homo sapiens

<400> SEQUENCE: 25
gttttcccag tcacgacgaa gttgatgatt gcaagaggtg                       40

<210> SEQ ID NO 26
<211> LENGTH: 41
<212> TYPE: DNA
<213> ORGANISM: Homo sapiens

<400> SEQUENCE: 26
aggaaacagc tatgaccatg gtttgtgcca tctactgcta t                     41

<210> SEQ ID NO 27
<211> LENGTH: 39
<212> TYPE: DNA
<213> ORGANISM: Homo sapiens

<400> SEQUENCE: 27
gttttcccag tcacgacgaa acgagtgccg ttgagcatg                        39

<210> SEQ ID NO 28
<211> LENGTH: 40
<212> TYPE: DNA
<213> ORGANISM: Homo sapiens

<400> SEQUENCE: 28
aggaaacagc tatgaccatg ctgacagtaa tggataccct                       40

<210> SEQ ID NO 29
<211> LENGTH: 41
<212> TYPE: DNA
<213> ORGANISM: Homo sapiens

<400> SEQUENCE: 29
gttttcccag tcacgacgga tttttttatct tcgacgagaa a                    41

<210> SEQ ID NO 30
<211> LENGTH: 42
<212> TYPE: DNA
<213> ORGANISM: Homo sapiens

<400> SEQUENCE: 30
aggaaacagc tatgaccatt tccccaagta agttatgcc at                     42

<210> SEQ ID NO 31
<211> LENGTH: 38
<212> TYPE: DNA
<213> ORGANISM: Homo sapiens -continued

```
<400> SEQUENCE: 31
gttttcccag tcacgacgtc ctgttggaca cagcggga                              38

<210> SEQ ID NO 32
<211> LENGTH: 39
<212> TYPE: DNA
<213> ORGANISM: Homo sapiens

<400> SEQUENCE: 32
aggaaacagc tatgaccatc atggccaaag gtgcttgaa                             39

<210> SEQ ID NO 33
<211> LENGTH: 22
<212> TYPE: DNA
<213> ORGANISM: Homo sapiens

<400> SEQUENCE: 33
ccacccacca cccaatcaga at                                               22

<210> SEQ ID NO 34
<211> LENGTH: 22
<212> TYPE: DNA
<213> ORGANISM: Homo sapiens

<400> SEQUENCE: 34
catctcgact aatggcacct cc                                               22

<210> SEQ ID NO 35
<211> LENGTH: 38
<212> TYPE: DNA
<213> ORGANISM: Homo sapiens

<400> SEQUENCE: 35
gttttcccag tcacgacgga gacagaggat ccagtgct                              38

<210> SEQ ID NO 36
<211> LENGTH: 39
<212> TYPE: DNA
<213> ORGANISM: Homo sapiens

<400> SEQUENCE: 36
aggaaacagc tatgaccatc cctgacggtg ctcccttca                             39

<210> SEQ ID NO 37
<211> LENGTH: 40
<212> TYPE: DNA
<213> ORGANISM: Homo sapiens

<400> SEQUENCE: 37
gttttcccag tcacgacgtt aacttggaaa acagcagtct                            40

<210> SEQ ID NO 38
<211> LENGTH: 41
<212> TYPE: DNA
<213> ORGANISM: Homo sapiens

<400> SEQUENCE: 38
aggaaacagc tatgaccatc atcaccacaa gaactgccat g                          41

<210> SEQ ID NO 39
<211> LENGTH: 40
<212> TYPE: DNA
<213> ORGANISM: Homo sapiens
```

```
<400> SEQUENCE: 39
gttttcccag tcacgacgac tctcctgaaa atgacagcat                    40

<210> SEQ ID NO 40
<211> LENGTH: 41
<212> TYPE: DNA
<213> ORGANISM: Homo sapiens

<400> SEQUENCE: 40
aggaaacagc tatgaccatt aaatgagatt cagtccacac t                  41

<210> SEQ ID NO 41
<211> LENGTH: 40
<212> TYPE: DNA
<213> ORGANISM: Homo sapiens

<400> SEQUENCE: 41
gttttcccag tcacgacgat aaatgactac acacctgcaa                    40

<210> SEQ ID NO 42
<211> LENGTH: 41
<212> TYPE: DNA
<213> ORGANISM: Homo sapiens

<400> SEQUENCE: 42
aggaaacagc tatgaccata acgatcatcc ccaagccatc t                  41

<210> SEQ ID NO 43
<211> LENGTH: 22
<212> TYPE: DNA
<213> ORGANISM: Homo sapiens

<400> SEQUENCE: 43
ctgagtacct gcttgaacag ag                                       22

<210> SEQ ID NO 44
<211> LENGTH: 22
<212> TYPE: DNA
<213> ORGANISM: Homo sapiens

<400> SEQUENCE: 44
gaccattgat ctctagaagc tc                                       22

<210> SEQ ID NO 45
<211> LENGTH: 41
<212> TYPE: DNA
<213> ORGANISM: Homo sapiens

<400> SEQUENCE: 45
gttttcccag tcacgacggg actattaata tagcaaaagg c                  41

<210> SEQ ID NO 46
<211> LENGTH: 40
<212> TYPE: DNA
<213> ORGANISM: Homo sapiens

<400> SEQUENCE: 46
aggaaacagc tatgaccatc agtgccatta ctcttccaga                    40

<210> SEQ ID NO 47
<211> LENGTH: 39
<212> TYPE: DNA
<213> ORGANISM: Homo sapiens
```

-continued

```
<400> SEQUENCE: 47
gttttcccag tcacgacgta cttatgtgcc tgcagaaca                    39

<210> SEQ ID NO 48
<211> LENGTH: 40
<212> TYPE: DNA
<213> ORGANISM: Homo sapiens

<400> SEQUENCE: 48
aggaaacagc tatgaccatc atgtttgatg aaaatgcccc                   40

<210> SEQ ID NO 49
<211> LENGTH: 39
<212> TYPE: DNA
<213> ORGANISM: Homo sapiens

<400> SEQUENCE: 49
gttttcccag tcacgacgat tgttggtgga cgagggatg                    39

<210> SEQ ID NO 50
<211> LENGTH: 40
<212> TYPE: DNA
<213> ORGANISM: Homo sapiens

<400> SEQUENCE: 50
aggaaacagc tatgaccatc catttcggca aaggctgaag                   40

<210> SEQ ID NO 51
<211> LENGTH: 39
<212> TYPE: DNA
<213> ORGANISM: Homo sapiens

<400> SEQUENCE: 51
gttttcccag tcacgacgca gagtcagagc cagagaagg                    39

<210> SEQ ID NO 52
<211> LENGTH: 40
<212> TYPE: DNA
<213> ORGANISM: Homo sapiens

<400> SEQUENCE: 52
aggaaacagc tatgaccata gaagctcagc tgcaatttgc                   40

<210> SEQ ID NO 53
<211> LENGTH: 21
<212> TYPE: DNA
<213> ORGANISM: Homo sapiens

<400> SEQUENCE: 53
caggcgagct gcatatgatt g                                      21

<210> SEQ ID NO 54
<211> LENGTH: 23
<212> TYPE: DNA
<213> ORGANISM: Homo sapiens

<400> SEQUENCE: 54
cctcctttga caatgtctga cac                                    23

<210> SEQ ID NO 55
<211> LENGTH: 41
<212> TYPE: DNA
<213> ORGANISM: Homo sapiens
```

```
<210> SEQ ID NO 55
<211> LENGTH: 41
<212> TYPE: DNA
<213> ORGANISM: Homo sapiens

<400> SEQUENCE: 55
gttttcccag tcacgacggt gtcttcatag tgggattga t                    41

<210> SEQ ID NO 56
<211> LENGTH: 40
<212> TYPE: DNA
<213> ORGANISM: Homo sapiens

<400> SEQUENCE: 56
aggaaacagc tatgaccatg aagctccaga tgttgcacat                     40

<210> SEQ ID NO 57
<211> LENGTH: 39
<212> TYPE: DNA
<213> ORGANISM: Homo sapiens

<400> SEQUENCE: 57
gttttcccag tcacgacgag agccaactgt tactacttc                      39

<210> SEQ ID NO 58
<211> LENGTH: 40
<212> TYPE: DNA
<213> ORGANISM: Homo sapiens

<400> SEQUENCE: 58
aggaaacagc tatgaccatt gaaggaacag cctgggaatc                     40

<210> SEQ ID NO 59
<211> LENGTH: 39
<212> TYPE: DNA
<213> ORGANISM: Homo sapiens

<400> SEQUENCE: 59
gttttcccag tcacgacgtt agccttctga agacagcaa                      39

<210> SEQ ID NO 60
<211> LENGTH: 40
<212> TYPE: DNA
<213> ORGANISM: Homo sapiens

<400> SEQUENCE: 60
aggaaacagc tatgaccatc atggataata atggcaccca                     40

<210> SEQ ID NO 61
<211> LENGTH: 39
<212> TYPE: DNA
<213> ORGANISM: Homo sapiens

<400> SEQUENCE: 61
gttttcccag tcacgacgtt tccaagggc gaacagggc                       39

<210> SEQ ID NO 62
<211> LENGTH: 41
<212> TYPE: DNA
<213> ORGANISM: Homo sapiens

<400> SEQUENCE: 62
aggaaacagc tatgaccatc caacaatact taatcctagg c                   41

<210> SEQ ID NO 63
<211> LENGTH: 23
<212> TYPE: DNA
<213> ORGANISM: Homo sapiens
```

<210> SEQ ID NO 64
<211> LENGTH: 22
<212> TYPE: DNA
<213> ORGANISM: Homo sapiens

<400> SEQUENCE: 64 cccccctacag ttttgaagac cc                                           22

<210> SEQ ID NO 65
<211> LENGTH: 40
<212> TYPE: DNA
<213> ORGANISM: Homo sapiens

<400> SEQUENCE: 65
gttttcccag tcacgacgaa gaggaggaag tgtgtgacac                         40

<210> SEQ ID NO 66
<211> LENGTH: 40
<212> TYPE: DNA
<213> ORGANISM: Homo sapiens

<400> SEQUENCE: 66
aggaaacagc tatgaccatg acaggctgcc ttcactcacc                         40

<210> SEQ ID NO 67
<211> LENGTH: 39
<212> TYPE: DNA
<213> ORGANISM: Homo sapiens

<400> SEQUENCE: 67
gttttcccag tcacgacgtc aaagctggtc cattccatt                          39

<210> SEQ ID NO 68
<211> LENGTH: 40
<212> TYPE: DNA
<213> ORGANISM: Homo sapiens

<400> SEQUENCE: 68
aggaaacagc tatgaccatg gatgtgccac agatggtgac                         40

<210> SEQ ID NO 69
<211> LENGTH: 39
<212> TYPE: DNA
<213> ORGANISM: Homo sapiens

<400> SEQUENCE: 69
gttttcccag tcacgacgat gatgcaccca actggagtt                          39

<210> SEQ ID NO 70
<211> LENGTH: 40
<212> TYPE: DNA
<213> ORGANISM: Homo sapiens

<400> SEQUENCE: 70
aggaaacagc tatgaccatg gctgccatat cctccaacta                         40

<210> SEQ ID NO 71
<211> LENGTH: 39
<212> TYPE: DNA
<213> ORGANISM: Homo sapiens -continued

```
<400> SEQUENCE: 71
gttttcccag tcacgacggg acctcctcaa tgtaagtct                    39

<210> SEQ ID NO 72
<211> LENGTH: 40
<212> TYPE: DNA
<213> ORGANISM: Homo sapiens

<400> SEQUENCE: 72
aggaaacagc tatgaccata ttgtcaggac cagtgcattc                   40
```